(12) United States Patent
Russell et al.

(10) Patent No.: US 10,385,392 B2
(45) Date of Patent: Aug. 20, 2019

(54) NUCLEIC ACID HYBRIDIZATION PROBES

(71) Applicant: Abbott Molecular Inc., Des Plaines, IL (US)

(72) Inventors: John C. Russell, Chicago, IL (US); Ekaterina Pestova, Glenview, IL (US)

(73) Assignee: ABBOTT MOLECULAR INC., Des Plaines, IL (US)

( * ) Notice: Subject to any disclaimer, the term of this patent is extended or adjusted under 35 U.S.C. 154(b) by 271 days.

(21) Appl. No.: 13/728,975

(22) Filed: Dec. 27, 2012

(65) Prior Publication Data

US 2013/0237437 A1    Sep. 12, 2013

Related U.S. Application Data

(60) Provisional application No. 61/582,135, filed on Dec. 30, 2011.

(51) Int. Cl.

| | | |
|---|---|---|
| *C12Q 1/6876* | (2018.01) | |
| *C12Q 1/6811* | (2018.01) | |
| *C12Q 1/6816* | (2018.01) | |
| *C12Q 1/682* | (2018.01) | |
| *C12Q 1/6855* | (2018.01) | |
| *C12N 15/10* | (2006.01) | |
| *C40B 30/04* | (2006.01) | |
| *C40B 40/06* | (2006.01) | |

(52) U.S. Cl.
CPC ....... *C12Q 1/6876* (2013.01); *C12N 15/1093* (2013.01); *C12Q 1/682* (2013.01); *C12Q 1/6811* (2013.01); *C12Q 1/6816* (2013.01); *C12Q 1/6855* (2013.01); *C40B 30/04* (2013.01); *C40B 40/06* (2013.01)

(58) Field of Classification Search
CPC ....... C40B 30/04; C40B 40/06; C12Q 1/6876; C12Q 1/6811
USPC .............. 435/6.11; 506/9, 16; 536/24.3
See application file for complete search history.

(56) References Cited

U.S. PATENT DOCUMENTS

| | | | |
|---|---|---|---|
| 6,261,770 B1 | 7/2001 | Warthoe | |
| 2002/0155456 A1 | 10/2002 | Pandian | |
| 2005/0059049 A1 | 3/2005 | Moen | |
| 2005/0118603 A1 | 6/2005 | Chun | |
| 2008/0057513 A1* | 3/2008 | Farrell | ............... 435/6 |
| 2008/0286835 A1 | 11/2008 | Hoser | |
| 2010/0248991 A1* | 9/2010 | Roesler et al. ...... C12Q 1/6844 | 506/16 |
| 2010/0330574 A1* | 12/2010 | Whitman et al. .... C12Q 1/6853 | 435/6.1 |
| 2011/0059431 A1 | 3/2011 | Mirkin | |

FOREIGN PATENT DOCUMENTS

| | | | | |
|---|---|---|---|---|
| JP | H0788000 A | 4/1995 | | |
| JP | 2001515362 A | 9/2001 | | |
| JP | 2005517900 A | 6/2005 | | |
| JP | 2007506431 A | 3/2007 | | |
| WO | 2008157649 A1 | 12/2008 | | |
| WO | WO 2008157649 A1 * | 12/2008 | ........... | C12Q 1/6832 |
| WO | 2010133849 A1 | 11/2010 | | |
| WO | 2011008530 A2 | 1/2011 | | |

OTHER PUBLICATIONS

Stratagene 1988 catalog (cover and p. 39).*
Takeshita et al., "Oligodeoxynucleotides Containing Synthetic Abasic Sites: Model substrates for DNA polymerases and apurinic/apyrimidinic endonucleases," J. Biol. Chem. 1987, 262:10171-10179.*
Heyduk et al., "Nucleic Acid-Based Fluorescence Sensors for Detecting Proteins," Anal. Chem. 2005, 77, 1147-1156.*
IDT product information regarding "Spacer 18", retrieved from IDT online Catalog using Internet <URL: https://www.idtdna.com/site/Catalog/Modifications/Product/1393>, retrieved on Dec. 29, 2016.*
Maan et al., "Rapid cDNA synthesis and sequencing techniques for the genetic study of bluetongue and other dsRNA viruses," J. Virol. Methods 2007, 143:132-139. (Year: 2007).*
International Search Report and Written Opinion of the International Search Authority dated Jun. 18, 2013 for PCT/US/2012/072144.
Office Action dated Nov. 22, 2016 for Japanese Patent Application No. 2014-550519, six pages.
EPO Communication for Application No. 12863875.6 dated Apr. 28, 2016, four pages.
European search report for Application No. 12863875.6 dated Sep. 15, 2016, five pages.
Takeshita et al., "Oligodeoxynucleotides Containing Synthetic Abasic Sites," J. Biol. Chem. 262(21):10171-10179 (1987).

* cited by examiner

*Primary Examiner* — Kaijiang Zhang
(74) *Attorney, Agent, or Firm* — Klintworth & Rozenblat IP LLP

(57) ABSTRACT

Compositions of nucleic acid hybridization probes for detecting a nucleic acid target sequence and methods for their production are described. In one preferred embodiment, the nucleic acid hybridization probe includes a hybridization domain, an adaptor, a linker, and a signaling domain. The hybridization domain includes a nucleic acid sequence having complementarity to the nucleic acid target sequence. The adaptor is a nucleic acid sequence. The linker includes a moiety having at least one abasic site, such that the moiety blocks extension by an elongating polymerase on a nucleic acid template containing the moiety. The signaling domain comprises a nucleic acid having at least one label or a nucleic acid having at least one nucleic acid domain for binding at least one additional nucleic acid.

22 Claims, 11 Drawing Sheets

Specification includes a Sequence Listing.

A

B

C

A

B

```
                            SEQUENCE LISTING

<160> NUMBER OF SEQ ID NOS: 20

<210> SEQ ID NO 1
<211> LENGTH: 99
<212> TYPE: DNA
<213> ORGANISM: Artificial Sequence
<220> FEATURE:
<223> OTHER INFORMATION: SYNTHETIC OLIGONUCLEOTIDE
<220> FEATURE:
<221> NAME/KEY: misc_feature
<222> LOCATION: (73)..(74)
<223> OTHER INFORMATION: Internucleotide spacer group (iSp9) located
      between nucleotide positions 73 and 74.

<400> SEQUENCE: 1
catgaacaat aactaagaca agttctgtat ctatgtctta ttctaaaact gatactgaga      60
ctttgtcaga atcggagatg agtggatggg agagaagtg                            99

<210> SEQ ID NO 2
<211> LENGTH: 98
<212> TYPE: DNA
<213> ORGANISM: Artificial Sequence
<220> FEATURE:
<223> OTHER INFORMATION: SYNTHETIC OLIGONUCLEOTIDE
<220> FEATURE:
<221> NAME/KEY: misc_feature
<222> LOCATION: (73)..(74)
<223> OTHER INFORMATION: Internucleotide spacer group (iSp9) located
      between nucleotide positions 73 and 74.

<400> SEQUENCE: 2
catgaacaat aactaagaca agttctgtat ctatgtctta ttctaaaact gatactgaga      60
ctttgtcaga atcgtggtag gagggatgaa tgtgagtg                             98

<210> SEQ ID NO 3
<211> LENGTH: 99
<212> TYPE: DNA
<213> ORGANISM: Artificial Sequence
<220> FEATURE:
<223> OTHER INFORMATION: SYNTHETIC OLIGONUCLEOTIDE
<220> FEATURE:
<221> NAME/KEY: misc_feature
<222> LOCATION: (81)..(82)
<223> OTHER INFORMATION: Internucleotide spacer group (iSp9) located
      between nucleotide positions 81 and 82.

<400> SEQUENCE: 3
gctctgatta tgccaccgtc cttgattgct ctgattatgc caccgtcctt gattgctctg      60
attatgccac cgtccttgat tgcgattccg acactcacc                            99

<210> SEQ ID NO 4
<211> LENGTH: 99
<212> TYPE: DNA
<213> ORGANISM: Artificial Sequence
<220> FEATURE:
<223> OTHER INFORMATION: SYNTHETIC OLIGONUCLEOTIDE
<220> FEATURE:
<221> NAME/KEY: misc_feature
<222> LOCATION: (81)..(82)
<223> OTHER INFORMATION: Internucleotide spacer group (iSp9) located
      between nucleotide positions 81 and 82.

<400> SEQUENCE: 4
```
gcctcgctcc agaccttgat accgtttgcc tcgctccaga ccttgatacc gtttgcctcg      60
ctccagacct tgataccgtt tgcgattccg acactcacc                             99

<210> SEQ ID NO 5
<211> LENGTH: 195
<212> TYPE: DNA
<213> ORGANISM: Artificial Sequence
<220> FEATURE:
<223> OTHER INFORMATION: SYNTHETIC OLIGONUCLEOTIDE

<400> SEQUENCE: 5
aagagctgag acggagtcag gagcaagagc tgagacggag tcaggagcaa gagctgagac      60
ggagtcagga gcaagagctg agacggagtc aggagcaaga gctgagacgg agtcaggagc     120
aagagctgag acggagtcag gagcaagagc tgagacggag tcaggagcaa tcaaggacgg     180
tggcataatc agagc                                                      195

<210> SEQ ID NO 6
<211> LENGTH: 195
<212> TYPE: DNA
<213> ORGANISM: Artificial Sequence
<220> FEATURE:
<223> OTHER INFORMATION: SYNTHETIC OLIGONUCLEOTIDE

<400> SEQUENCE: 6
tggtgctagt tctggagctt gtgctggtgc tagttctgga gcttgtgctg gtgctagttc      60
tggagcttgt gctggtgcta gttctggagc ttgtgctggt gctagttctg gagcttgtgc     120
tggtgctagt tctggagctt gtgctggtgc tagttctgga gcttgtgcaa acggtatcaa     180
ggtctggagc gaggc                                                      195

<210> SEQ ID NO 7
<211> LENGTH: 45
<212> TYPE: DNA
<213> ORGANISM: Artificial Sequence
<220> FEATURE:
<223> OTHER INFORMATION: SYNTHETIC OLIGONUCLEOTIDE
<220> FEATURE:
<221> NAME/KEY: misc_feature
<222> LOCATION: (27)..(28)
<223> OTHER INFORMATION: Internucleotide spacer group (iSp9) located
      between nucleotide positions 27 and 28.

<400> SEQUENCE: 7
aatcaaggac ggtggcataa tcagagcgcg attccgacac tcacc                      45

<210> SEQ ID NO 8
<211> LENGTH: 45
<212> TYPE: DNA
<213> ORGANISM: Artificial Sequence
<220> FEATURE:
<223> OTHER INFORMATION: SYNTHETIC OLIGONUCLEOTIDE
<220> FEATURE:
<221> NAME/KEY: misc_feature
<222> LOCATION: (27)..(28)
<223> OTHER INFORMATION: Internucleotide spacer group (iSp9) located
      between nucleotide positions 27 and 28.

<400> SEQUENCE: 8
aaacggtatc aaggtctgga gcgaggcgcg attccgacac tcacc                      45

<210> SEQ ID NO 9
<211> LENGTH: 53
<212> TYPE: DNA

```
<213> ORGANISM: Artificial Sequence
<220> FEATURE:
<223> OTHER INFORMATION: SYNTHETIC OLIGONUCLEOTIDE
<220> FEATURE:
<221> NAME/KEY: misc_feature
<222> LOCATION: (27)..(28)
<223> OTHER INFORMATION: Internucleotide spacer group (iSp9) located
      between nucleotide positions 27 and 28.

<400> SEQUENCE: 9
aatcaaggac ggtggcataa tcagagcgga gatgagtgga tgggagagaa gtg          53

<210> SEQ ID NO 10
<211> LENGTH: 52
<212> TYPE: DNA
<213> ORGANISM: Artificial Sequence
<220> FEATURE:
<223> OTHER INFORMATION: SYNTHETIC OLIGONUCLEOTIDE
<220> FEATURE:
<221> NAME/KEY: misc_feature
<222> LOCATION: (27)..(28)
<223> OTHER INFORMATION: Internucleotide spacer group (iSp9) located
      between nucleotide positions 27and 28.

<400> SEQUENCE: 10
aatcaaggac ggtggcataa tcagagcgtg gtaggaggga tgaatgtgag tg           52

<210> SEQ ID NO 11
<211> LENGTH: 20
<212> TYPE: DNA
<213> ORGANISM: Artificial Sequence
<220> FEATURE:
<223> OTHER INFORMATION: SYNTHETIC OLIGONUCLEOTIDE
<220> FEATURE:
<221> NAME/KEY: misc_feature
<222> LOCATION: (1)..(1)
<223> OTHER INFORMATION: 5'-phosphate at terminus of nucleotide 1.

<400> SEQUENCE: 11
ggtgagtgtc ggaatcgcag                                               20

<210> SEQ ID NO 12
<211> LENGTH: 22
<212> TYPE: DNA
<213> ORGANISM: Artificial Sequence
<220> FEATURE:
<223> OTHER INFORMATION: SYNTHETIC OLIGONUCLEOTIDE

<400> SEQUENCE: 12
atctgcgatt ccgacactca cc                                            22

<210> SEQ ID NO 13
<211> LENGTH: 22
<212> TYPE: DNA
<213> ORGANISM: Artificial Sequence
<220> FEATURE:
<223> OTHER INFORMATION: SYNTHETIC OLIGONUCLEOTIDE
<220> FEATURE:
<221> NAME/KEY: misc_feature
<222> LOCATION: (1)..(1)
<223> OTHER INFORMATION: 5'-TET at terminus of nucleotide 1.

<400> SEQUENCE: 13
atctgcgatt ccgacactca cc                                            22

<210> SEQ ID NO 14
<211> LENGTH: 20
<212> TYPE: DNA
<213> ORGANISM: Artificial Sequence
```

```
<220> FEATURE:
<223> OTHER INFORMATION: SYNTHETIC SEQUENCE
<220> FEATURE:
<221> NAME/KEY: misc_feature
<222> LOCATION: (1)..(1)
<223> OTHER INFORMATION: 5'-phosphate at terminus of nucleotide 1.

<400> SEQUENCE: 14
gcagttcggc agaatcaggc                                              20

<210> SEQ ID NO 15
<211> LENGTH: 22
<212> TYPE: DNA
<213> ORGANISM: Artificial Sequence
<220> FEATURE:
<223> OTHER INFORMATION: SYNTHETIC OLIGONUCLEOTIDE

<400> SEQUENCE: 15
ttgcctgatt ctgccgaact gc                                           22

<210> SEQ ID NO 16
<211> LENGTH: 22
<212> TYPE: DNA
<213> ORGANISM: Artificial Sequence
<220> FEATURE:
<223> OTHER INFORMATION: SYNTHETIC OLIGONUCLEOTIDE
<220> FEATURE:
<221> NAME/KEY: misc_feature
<222> LOCATION: (1)..(1)
<223> OTHER INFORMATION: 5'-TET at terminus of nucleotide position 1.

<400> SEQUENCE: 16
ttgcctgatt ctgccgaact gc                                           22

<210> SEQ ID NO 17
<211> LENGTH: 36
<212> TYPE: DNA
<213> ORGANISM: Artificial Sequence
<220> FEATURE:
<223> OTHER INFORMATION: SYNTHETIC OLIGONUCLEOTIDE

<400> SEQUENCE: 17
ggagatgagt ggatgggaga gaagtgaggt tgagtg                            36

<210> SEQ ID NO 18
<211> LENGTH: 10
<212> TYPE: DNA
<213> ORGANISM: Artificial Sequence
<220> FEATURE:
<223> OTHER INFORMATION: SYNTHETIC OLIGONUCLEOTIDE

<400> SEQUENCE: 18
cactcaacct                                                         10

<210> SEQ ID NO 19
<211> LENGTH: 36
<212> TYPE: DNA
<213> ORGANISM: Artificial Sequence
<220> FEATURE:
<223> OTHER INFORMATION: SYNTHETIC OLIGONUCLEOTIDE

<400> SEQUENCE: 19
gtggtaggag ggatgaatgt gagtgtgaga atggag                            36

<210> SEQ ID NO 20
<211> LENGTH: 10
<212> TYPE: DNA
```

```
<213> ORGANISM: Artificial Sequence
<220> FEATURE:
<223> OTHER INFORMATION: SYNTHETIC OLIGONUCLEOTIDE

<400> SEQUENCE: 20
ctccattctc                                                            10
```

NUCLEIC ACID HYBRIDIZATION PROBES

CROSS-REFERENCE TO RELATED APPLICATIONS

This application claims benefit of priority under 35 U.S.C. 119 to U.S. provisional patent application Ser. No. 61/582,135, filed Dec. 30, 2011, and entitled "NUCLEIC ACID HYBRIDIZATION PROBES," the contents of which are herein incorporated by reference in its entirety.

SEQUENCE LISTING

The SEQ ID NOs. disclosed herein are included in the Sequence Listing found at the end of the specification and are included in a computer readable form entitled "ABT01-099-US [SEQUENCE LISTING]_ST25.text," filed by electronic means via the EFS-Web e-filing system, the contents of which are incorporated by reference in its entirety.

BACKGROUND OF THE INVENTION

Nearly all nucleic acid detection systems rely upon the use of nucleic acid hybridization probes. The applications of nucleic acid hybridization probes are well recognized in numerous fields, including medical diagnostics, molecular medicine, forensic science, specimen and organism cataloging and microbial pathogen epidemiology. The challenges in designing nucleic acid hybridization probes have remained the same in nearly all applications, namely achieving probe designs having high affinity and specificity for a given target and displaying high signal specific activity for identifying the target.

Whole genome screening methodologies using nucleic acid hybridization probes illustrate these challenges. In particular, chromosomal screening to identify nucleic acid targets in both a sequence-specific and chromosome-specific manner poses the greatest challenge for nucleic acid hybridization probe design. One such method, fluorescence in situ hybridization (FISH), uses nucleic acid hybridization probes having both superior targeting specificity and high signal specific activity to visualize the location of nucleic acid targets within a chromosomal spread. Thus, probes that may otherwise be suitable for other hybridization applications may not be necessarily appropriate for FISH applications.

Methods of preparing nucleic acid hybridization probes for FISH applications are well known in the art. For short probes prepared through chemical synthesis (e.g., single copy probes having a length less than 200 nucleotides), the probes are synthesized that contain labels or moieties that may be subsequently reacted with labels. Alternatively, such probes have been post-labeled following their synthesis using any suitable enzymatic or chemical means.

Long probes, such as those having a length from 200 bp to 500 kbp have been prepared in numerous ways. Nucleic acid substrates for long probes have been fragmented using sonication or restriction enzyme digestion. The resultant fragment population can be chemically modified to incorporate a suitable label.

Alternatively, the fragment population can be enzymatically labeled with nucleotide triphosphate analogs that contain a label or a moiety for reacting with a label. Suitable enzymatic labeling procedures have included internal labeling methods or terminal labeling methods. Known examples of internal labeling methods include polymerase-mediated techniques, such as nick-translation protocols, random priming methods, and the polymerase chain reaction. Known terminal labeling methods include polynucleotide kinase methods, ligase techniques and terminal transferase procedures.

Nucleic acid hybridization probes are typically composed of DNA or DNA analogs, such as PNA. RNA has also served as nucleic acid hybridization probes, owing to the fact that RNA transcripts can be produced in high yield as single-stranded molecules. Yet RNA-based probes often suffer in quality and reproducibility, owing to their sensitivity to nucleolytic degradation in biological specimens used in FISH assays.

Nucleic acids used for long probes are usually maintained in cloning vectors. For example, vector-borne nucleic acids are typically propagated in bacterial cultures. Typical harvests of such nucleic acids are relatively inefficient from such cultures. Thus, considerable time and expense is required to maintain a source of material for long probes.

Furthermore, prior art nucleic acid hybridization probes for FISH applications usually lack robust signal generating capability. This is attributed in part to the inherently low specific activity of label incorporation into a probe in relation to the suitability of the probe for hybridization in FISH assays. A high number of labels incorporated into a given nucleic acid can result in signal reduction due to internal quenching as well as lower hybridization specificity of the resultant probe. Moreover, a very long probe is often needed to place sufficient signal on a target nucleic acid. Yet as the length of such probes increase (holding probe mass constant), the concentration of each individual segment decreases. Thus, longer probes require longer incubation times for each hybridization segment to hybridize to its complement sequence within the nucleic acid target.

Thus, there is a need in the art for improved nucleic acid hybridization probes, both from the standpoint of improved production yields and probe designs having superior signal generating capability.

BRIEF SUMMARY OF THE INVENTION

In a first aspect, the invention is a nucleic acid hybridization probe for detecting a nucleic acid target sequence. The nucleic acid hybridization probe includes a hybridization domain, an adaptor, a linker, and a signaling domain. The hybridization domain comprises a nucleic acid sequence having complementarity to the nucleic acid target sequence. The adaptor comprises a nucleic acid sequence. The linker comprises a moiety having at least one abasic site, such that the moiety blocks extension by an elongating polymerase on a nucleic acid template containing the moiety. The signaling domain comprises a nucleic acid having at least one label or a nucleic acid having at least one nucleic acid domain for binding at least one additional nucleic acid.

In a second aspect, the invention is a nucleic acid hybridization probe for detecting a nucleic acid target sequence. The nucleic acid hybridization probe includes a hybridization domain, an adaptor, a linker and a signaling domain. The hybridization domain comprises a nucleic acid sequence having complementarity to the nucleic acid target sequence. The adaptor comprises a nucleic acid sequence. The linker comprises a moiety having at least one abasic site, such that the moiety blocks extension by an elongating polymerase on a nucleic acid template containing the moiety. The signaling domain comprises a labeled nucleic acid.

In a third aspect, the invention is a nucleic acid hybridization probe system for detecting a nucleic acid target. The nucleic acid hybridization probe system includes a first oligonucleotide, a second oligonucleotide, a third oligonucleotide, a fourth oligonucleotide, and a ligase. The first oligonucleotide comprises a single-stranded molecule having a first hybridization subdomain and a first signal acceptor subdomain. The second oligonucleotide comprises a single-stranded molecule having a second hybridization subdomain and a second signal acceptor subdomain. The third oligonucleotide comprises a single-stranded molecule having a first signal subdomain. The fourth oligonucleotide comprises a single-stranded molecule having a second signal subdomain. The first hybridization subdomain and the second hybridization domain together comprises a contiguous hybridization domain for binding to a contiguous complementary sequence of the nucleic acid sequence target. The first signal acceptor subdomain and the second signal acceptor subdomain when annealed together comprises a signal acceptor domain having double-stranded form with a signal domain binding site comprising a single-stranded form at the terminus of the signal acceptor domain. The first signal subdomain and the second signal subdomain when annealed together comprises a signal domain having double-stranded form with a signal acceptor domain-binding site comprising a single-stranded form at the terminus of the signal domain. The signal acceptor domain binding site and the signal domain-binding site each comprises a complementary sequence capable of being ligated together in the presence of the ligase.

In a fourth aspect, the invention is a method of preparing a nucleic acid hybridization probe for detecting a nucleic acid sequence target. The said method includes the following steps: fragmenting a nucleic acid comprising the nucleic acid sequence target to generate a population of double-stranded fragments; flushing the termini of the population of double-stranded fragments to generate a population of flush-ended fragments; ligating sequences comprising an adaptor onto each member of the population of flushed-ended fragments to generate a population of fragments containing terminal adaptor sequences; optionally size-fractionating the population via gel electrophoresis to obtain a template library restricted to the size range desired; subjecting the population of fragments containing terminal adaptor sequences to DNA amplification with a primer to generate a population of double-stranded molecules having a 5' single-stranded terminus; and denaturing the population of double-stranded molecules having a 5' single-stranded terminus to generate a population comprising the nucleic acid hybridization probe. The primer comprises a single-stranded molecule having the following structure: 5'-S-L-A-3', wherein S comprises a signaling domain, L comprises a linker and A comprises an adaptor. The signaling domain comprises a nucleic acid having at least one label or a nucleic acid having at least one nucleic acid domain for binding at least one additional nucleic acid. The linker comprises a moiety having at least one abasic site, such that the moiety blocks extension by an elongating polymerase on a nucleic acid template containing the moiety. The adaptor comprises a nucleic acid sequence corresponding to the adaptor sequence at the terminus of each member of the population of fragments containing terminal adaptor sequences and having the appropriate strand polarity to permit primer extension on the population of fragments containing terminal adaptor sequences using DNA amplification.

BRIEF DESCRIPTION OF THE DRAWINGS

In FIG. 3B, structure 100 is hybridized to a target DNA.

DETAILED DESCRIPTION OF THE INVENTION

The invention provides improved nucleic acid hybridization probes. The invention is drawn to nucleic acid hybridization probes having improved production yields. Furthermore, the invention is directed to robust probe designs having superior signal generating capability. The invention provides examples of nucleic acid hybridization probes for use in FISH applications. One skilled in the art, however, will recognize that the invention has broad applicability to all forms of nucleic acid detection that use nucleic acid hybridization probes.

Probe Design and Operative Principles

Figure 1:
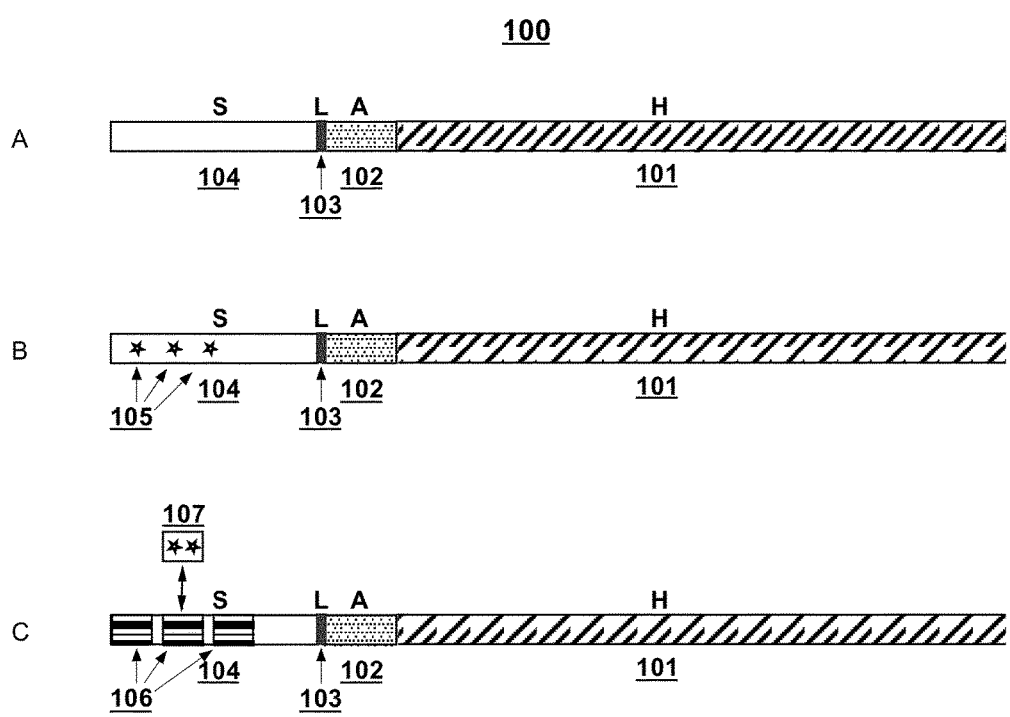
FIG. 1A illustrates one embodiment, wherein structure 100 is a nucleic acid hybridization probe. The 3' portion of 100 is the hybridization domain H (101) that hybridizes to the target nucleic acid sequence (not shown). Structure 100 also includes an adaptor A (102), a linker L (103), and a signaling domain S (104). The structure and function of 102 and 103 are described in detail below.
FIG. 1B illustrates one embodiment of structure 100 that contains a plurality of labels incorporated into 104 (denoted by asterisks).
FIG. 1C illustrates one embodiment of structure 100 that contains a plurality of binding sites 106 for binding to another nucleic acid 107 that is optionally labeled (denoted by asterisks). The double-ended arrow represents nucleic sequence complementarities for hybridization between 106 and 107.

Referring to FIG. 1A, nucleic acid hybridization probes having structure 100 represents a preferred embodiment. Structure 100 includes a hybridizing domain H (101) adaptor A (102) linker L (103) and signaling domain S (104). The hybridizing domain H represents the nucleic acid sequence that hybridizes to the desired target site. Adaptor A represents an artificial nucleic sequence that is covalently attached to the end of hybridization domain H. Linker L represents a moiety that serves to terminate or block extension by an elongating DNA polymerase. Signaling domain S represents a nucleic acid sequence that contains a label or which hybridizes to another nucleic acid that contains a label.

Hybridizing domain H (101) can have a length from about 50 nucleotides to about 5,000 nucleotides. Preferred lengths of 101 range from about 150 nucleotides to about 500 nucleotides. Highly preferred lengths of 101 range from about 200 nucleotides to about 350 nucleotides. As will be explained in greater detail below, these ranges are preferred for 101 in part due to the manner whereby 100 is generated.

Adaptor A (102) can have a length from about 15 nucleotides to about 30 nucleotides. Preferred lengths of 102 range from about 18 nucleotides to about 25 nucleotides. For many embodiments of 100, 102 represents a nucleic acid sequence unrelated to 101 and is not found naturally linked to nucleic acid sequences of 101, to the extent that those sequences or their complements are found in target nucleic acids. In this regard, 102 is an artificial nucleic acid wherein one may specify the precise sequence by design. As will be explained in greater detail below, 102 can have sequences in common with sequences of naturally occurring nucleic acids adjacent to the sequences of 101 in certain embodiments of 100.

Linker L (103) represents a moiety that blocks or terminates extension by an elongating DNA polymerase when the polymerase is synthesizing complementary strand nucleic acid from a template that includes 103. Accordingly, a polymerase will terminate synthesis of complementary strand nucleic acid upon encountering 103 in the template strand. The resultant complementary strand product will have a 3'-terminus adjacent to the site that contains 103 in the template strand.

Any moiety capable of blocking or terminating extension by an elongating polymerase on the complementary strand is suitable for use in 103. Such moieties are well known in the art and include spacers lacking bases (e.g., abasic sites). Preferred moieties are those that may be incorporated during chemical syntheses of nucleic acids using established synthetic nucleic acid chemistries (e.g., phosphoramidite chemistries). Examples of preferred moieties include spacers designated as iSp1, iSp3, iSp9 and iSp18 (Integrated DNA Technologies, Coralville, Iowa). A plurality of iSp1 or iSp3 spacers may be used for 103 to achieve the same polymerase blocking effects as observed with the longer spacers, iSp9 and iSp18. For the reasons explained below, the longer spacers (iSp9 and iSp18) are preferred over the shorter spacers (iSp1 and iSp3) for inclusion in 103. A highly preferred moiety for 103 is iSp9.

The signaling domain S (104) represents a nucleic acid sequence that includes at least one label (see FIG. 1B) or that serves as a hybridization site for another nucleic acid that includes at least one label (see FIG. 1C). Preferred lengths of 104 range from about 18 nucleotides to about 180 nucleotides. Highly preferred lengths of 104 range from about 25 nucleotides to about 150 nucleotides.

Referring to FIG. 1B, a preferred embodiment of 104 includes at least one label 105. More preferably, 104 includes a plurality of labels. Specifically, 104 includes a plurality of labels, wherein a label is distributed once every 3-12 nucleotides. Most preferably, 104 includes a plurality of labels, wherein a label is distributed once every 6 nucleotides.

Referring to FIG. 1C, a preferred embodiment of 104 includes a plurality of binding sites 106. For such an embodiment, 106 serves as a binding site for at least one other nucleic acid 107 that is labeled. When 104 is composed of a plurality of 106, a preferred number of 106 ranges from 2-10, depending upon the length of 106 and the lengths of 102 and 103. Preferred lengths of 106 range from about 10 nucleotides to about 40 nucleotides. Highly preferred lengths of 106 range from about 18 nucleotides to about 30 nucleotides.

A nucleotide-equivalent chemical unit represents a discrete synthetic, building block, unit for chemically synthesizing a synthetic oligonucleotide using conventional nucleic acid synthetic chemistries, such as phosphoramidite-based chemistries. In certain embodiments, structure 100 will have 101, 102, 103 and 104, wherein the sum of 102, 103 and 104 is preferably less than about 200 nucleotide-equivalent chemical units.

Consider the following example for illustrative purposes. A 102 having a nucleic acid sequence of 25 nucleotides would correspond to 25 nucleotide-equivalent chemical units. A 103 having a single iSp9 moiety would represent one nucleotide-equivalent chemical unit. A 104 having three copies of 106, wherein each 106 is composed of a nucleic acid sequence having 25 nucleotides, would correspond to 75 nucleotide-equivalent chemical units. For an example of 100 having the described 102, 103 and 104, the sum of elements 102, 103 and 104 corresponds to 101 nucleotide-equivalent chemical units. Because the practical limit of the present state of the art methods for accomplishing chemical synthesis of nucleic acids is about 200 nucleotide-equivalent chemical units, the sum of elements 102, 103 and 104 is preferably less than this value.

As mentioned above, element 103 is preferably a single nucleotide-equivalent chemical unit. While element 103 may be composed of a plurality of iSp1 or iSp3 spacers, selection of a longer spacer (e.g., iSp9 or iSp18) is preferred for economy and probe design considerations.

Figure 2:
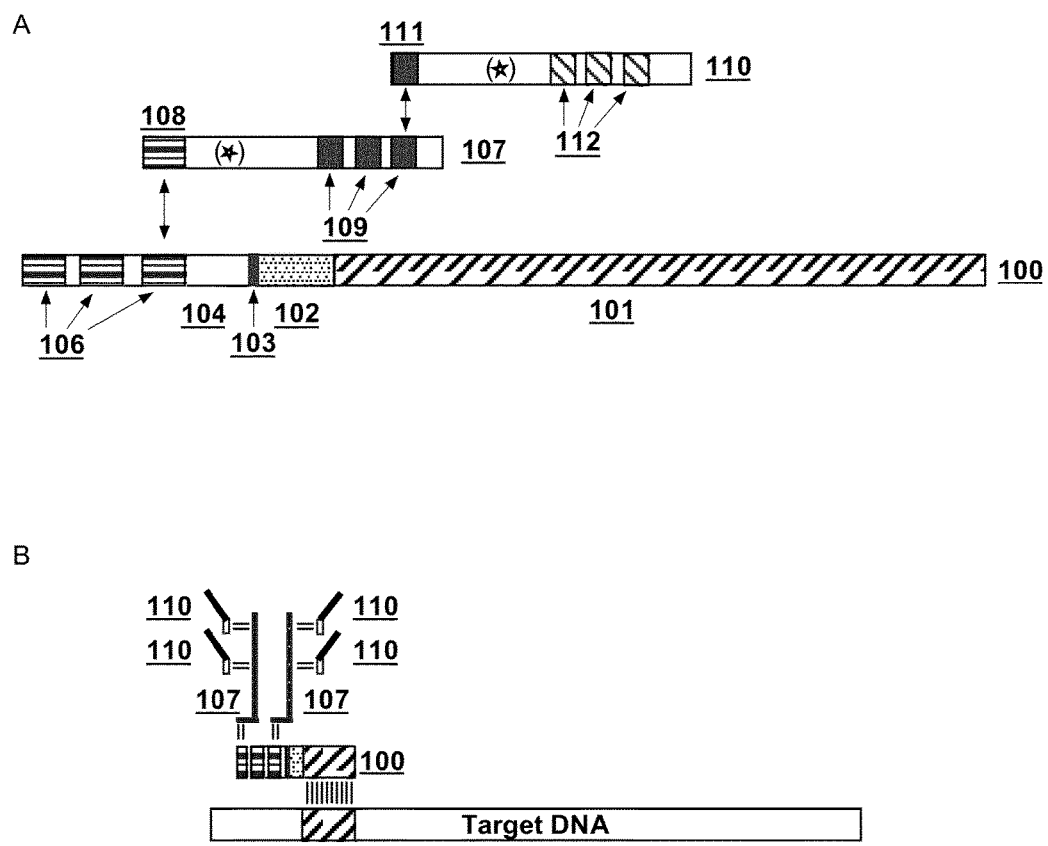
FIG. 2A illustrates one embodiment of structure 100 and interactions with additional nucleic acids 107 and 110. Each of 107 and 110 can include labels (denoted by asterisks). The double-ended arrows represent nucleic sequence complementarities for hybridization between different molecule strands.
FIG. 2B illustrates one embodiment of a branched hybridization network formed between 100, 107 and 110 when 100 is hybridized to a nucleic acid sequence target. The small lines represent nucleic sequence complementarities for hybridization between different molecule strands.

Referring to FIG. 2A, a preferred embodiment of 107 is a singled-stranded nucleic acid molecule. In general, 107 has a length ranging from about 25 nucleotides to about 200 nucleotides. According to this embodiment, 107 includes 108 corresponding to the specific pairing partner of one or more 106. Preferred lengths of 108 range from about 10 nucleotides to about 40 nucleotides. Highly preferred lengths of 108 range from about 18 nucleotides to about 30 nucleotides.

In some embodiments, 107 is labeled directly. Optionally, or alternatively, 107 includes a plurality of 109 that is labeled directly or that serves as a binding site for at least one additional nucleic acid that is labeled (110). In such embodiments, each 109 has a preferred length from about 25 nucleotides to about 40 nucleotides.

A 110 includes 111 corresponding to the pairing partner of one or more of 109. Accordingly 111 has a preferred length that is similar to the length of 109, or a length from about 25 nucleotides to about 40 nucleotides. Element 110 can be labeled directly. Optionally, or alternatively, 110 may include a plurality of sequence 112 that is labeled directly or that serves as binding sites for at least one additional nucleic acid that is labeled. The preferred length of each 112 ranges from about 25 nucleotides to about 40 nucleotides.

Signal amplification occurs through formation of a branched hybridization network formed between 100 with a plurality of 107 and 110 by virtue of the pairing interactions formed between 106 and 108 and between 109 and 111. More extensive hybridization networking is possible where additional single-stranded nucleic acids are designed based upon these pairwise hybridization interactions and variations of the same fall within the scope of the present invention.

Figure 3:
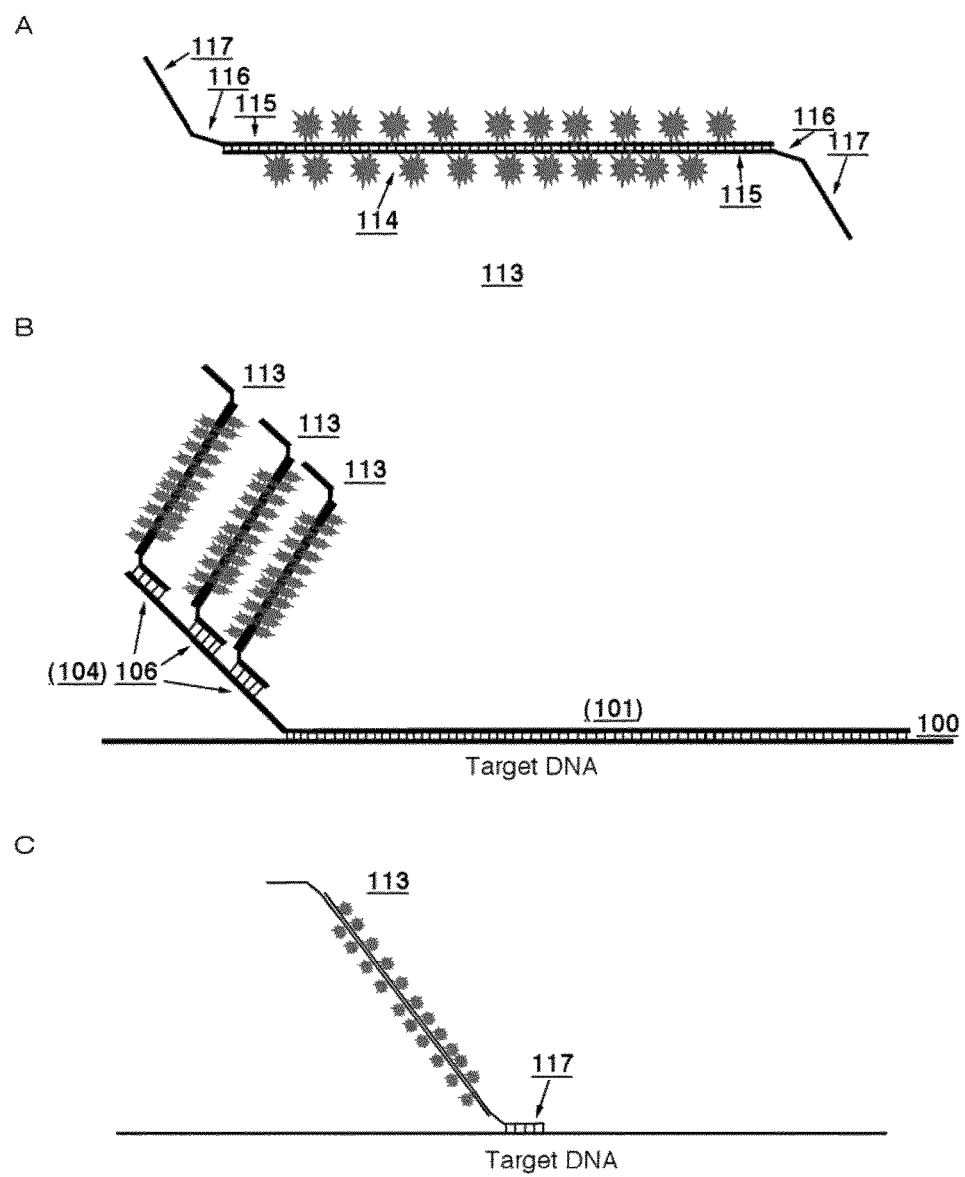
FIG. 3A illustrates another embodiment, wherein nucleic acid hybridization probe 113 is illustrated as a double-stranded form having 5' single-stranded termini (denoted by 117).
FIG. 3B illustrates one embodiment, wherein molecules can be used to hybridize via 117 to 104 or to a plurality of 106 present in 104 for structure 100.
FIG. 3C illustrates in an alternative embodiment that structure 113 can be used directly as a hybridization probe to detect a nucleic acid sequence target, wherein 117 within structure 113 has sequence complementarity to the target DNA.

FIG. 3 provides another embodiment of the nucleic acid hybridization probe. Referring to FIG. 3A, the nucleic acid hybridization probe is composed of a partially double-stranded nucleic acid 113. A 113 includes a duplexed DNA (114), an adaptor (115), a linker (116) and a single-stranded binding region (117).

A 114 is preferably internally labeled and serves as the signaling portion of 113. A 115 represents an artificial nucleic sequence that is covalently attached to the end of 114. A 116 represents a moiety that serves to terminate or block extension by an elongating DNA polymerase. Single-stranded binding region (117) represents a nucleic acid sequence that hybridizes to another nucleic acid sequence.

Referring to FIG. 3B, 113 represents the at least one additional nucleic acid that binds to 100 to provide signal detection. In this application, 117 binds to 104 or to one or more copies of 106 located in 104 of structure 100. In such applications, 117 has a preferred length ranging from about 25 to 40 nucleotides.

Referring to FIG. 3C, structure 113 serves as a nucleic acid hybridization probe to directly detect a nucleic acid sequence target. In this application, structure 100 is not required because structure 113 serves the same function as structure 100. In this embodiment, 117 of structure 113 performs the same functions as the hybridization domain H (101) of structure 100; i.e., 117 represents nucleic acid sequences that hybridizes to the desired nucleic acid sequence target. In such applications, the preferred length of 117 ranges from 50 nucleotides to 180 nucleotides.

A 114 has the same length criteria as described previously for 101. A 114 can be either a natural sequence or an artificial sequence having a defined sequence composition.

The design criteria for 115, 116 and 117 follow the design considerations discussed previously for 102, 103 and 104, respectively.

The principle whereby a nucleic acid target is detected with 100 and 113 is illustrated in FIG. 3B. Without being bound to any particular theory about the order of reaction, the following illustrates the operative principle. Structure 100 hybridizes to the nucleic acid target region via interactions with 101. At least one 113 hybridizes with 100 via interactions between 117 and 104. Where 104 includes a plurality of 106, a plurality of 113 hybridizes to 100 via interactions of each 117 with each 106. In this latter example, signal amplification results upon binding of a plurality of 113 to the nucleic acid target via structure 100. The target nucleic acid is detected by the signal in 114.

Figure 4:
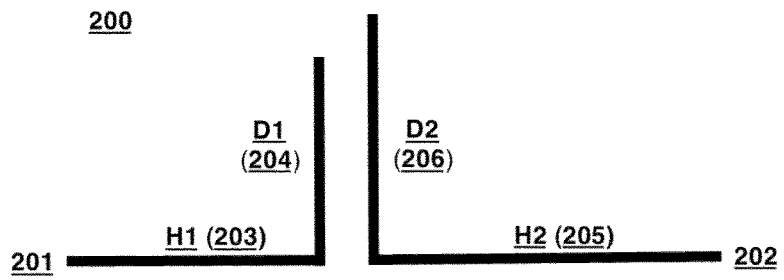
FIG. 4A illustrates components of a nucleic acid hybridization probe system 200 that includes 201 and 202.
FIG. 4B illustrates one embodiment whereby 200 interacts with a nucleic acid target T (207). Structures 204 and 206 form a duplex comprising D1:D2 of 200, and structures 203 and 205 form hybridization structures H1 and H2, respectively with target 207.
FIG. 4C illustrates a signaling domain 209 comprising 210 and 211, wherein 210 and 211 are labeled.
FIG. 4D illustrates another embodiment of 200 wherein structures 201, 201', 202, and 202' represent different nucleic acid hybridization probe components for structures 200 and 200', respectively. Oligonucleotides 204c and 206c are complementary nucleic acids that hybridize to all or part of nucleic acid hybridization probe components 204 and 206 (not denoted in FIG. 4D), respectively, of structures 200 and 200' during the initial annealing of 200 and 200' to the nucleic acid sequence target T, 207.
FIG. 4E illustrates the principle of operation for components of the system that includes a ligase-competent substrate between 200, 209, target T (207), wherein a sporadically bound probe, such as 202 illustrated with minimal base-pairing interactions with the nucleic acid sequence target, will not form the requisite substrate for a ligase (e.g., a hybrid formed between 208 and 212).
Figure 4:
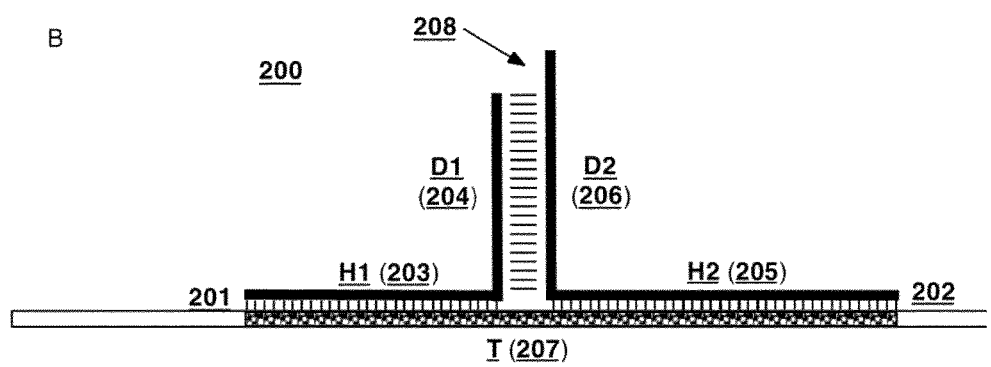
Figure 4:
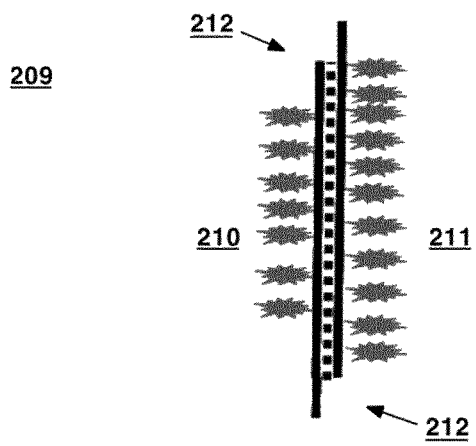
Figure 4:
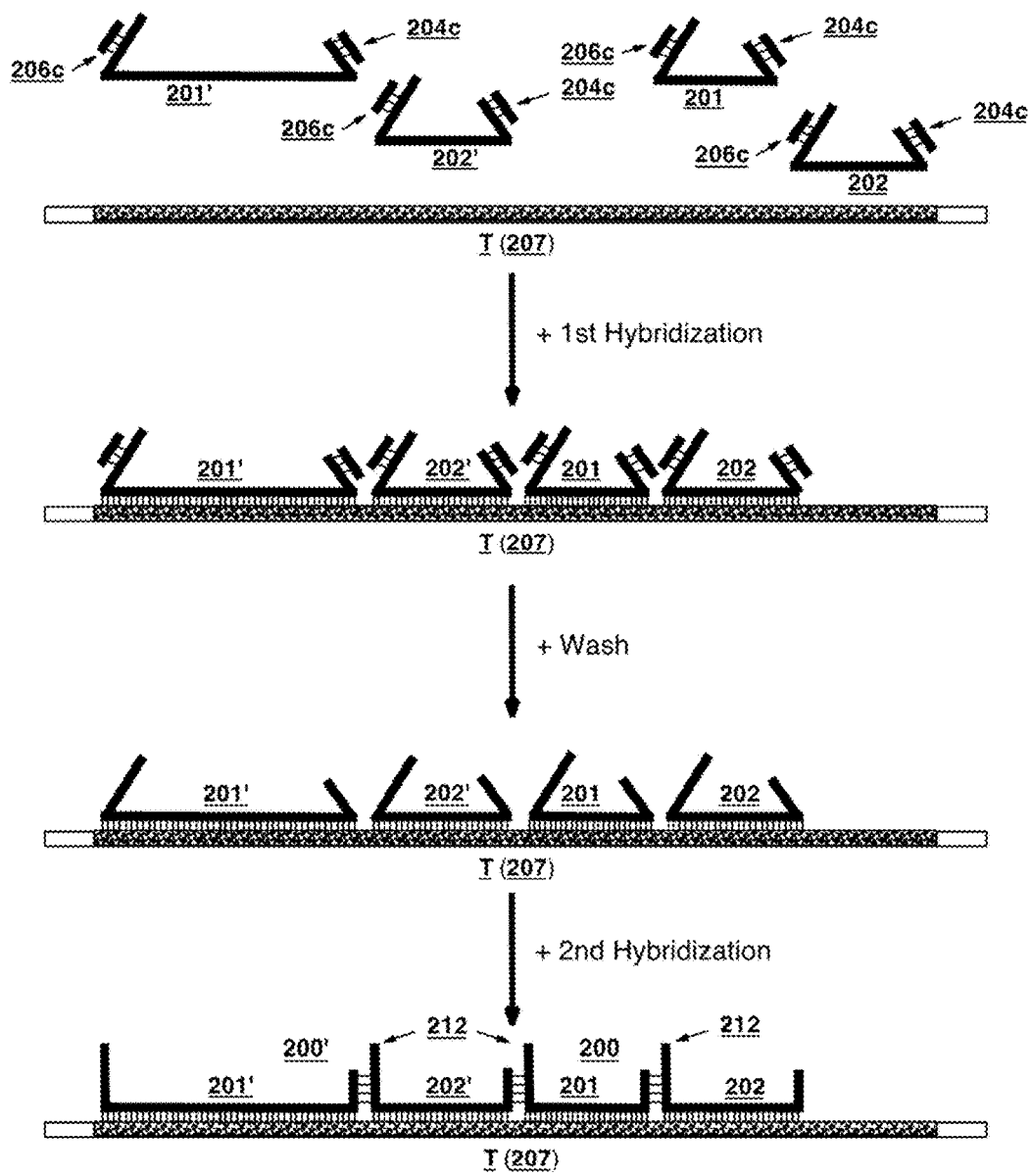

Referring to FIG. 4, a nucleic acid hybridization probe having structure 200 represents a preferred embodiment. Referring to FIG. 4A, 200 is a bipartite structure having 201 and 202. A 201 includes a hybridization subdomain H1 (203) and a signaling acceptor subdomain D1 (204). A 202 includes a hybridization subdomain H2 (205) and a signaling acceptor subdomain D2 (206).

Depending upon the source of 203 and 205, their preferred lengths range from about 25 nucleotide to about 300 nucleotides. If 203 and 205 are prepared as part of 201 and 202, respectively, with synthetic oligonucleotide chemistry, then the preferred lengths of 203 and 205 range from about 25 nucleotides to about 180 nucleotides. If 203 and 205 are prepared from a source of the nucleic acid sequence target with the procedures described below, then the preferred lengths of 203 and 205 range from about 100 nucleotides to about 300 nucleotides. Preferred lengths for 203 and 205 range from 18-40 nucleotides.

Referring to FIG. 4B, 203 and 205 hybridize to a continuous segment of nucleic acid target T (207). Nucleic acids 204 and 206 are complementary except for the presence of a terminal single-stranded sequence (208) at the terminus of the resultant duplex formed between 204 and 206. The element 208 corresponds to a single-stranded sequence having a preferred length from 1-6 nucleotides. Element 208 serves as a ligation site for a signaling domain S (209).

Referring to FIG. 4C, 209 has two complementary strands 210 and 211). Nucleic acids 210 and 211 have preferred lengths ranging from about 25 nucleotides to 10,000 nucleotides. Where 210 and 211 are prepared with synthetic oligonucleotide chemistries, the lengths of 210 and 211 range from about 25 nucleotides to about 200 nucleotides. Highly preferred lengths of 210 and 211 as synthetic oligonucleotides fall within the range from about 50 nucleotides to about 150 nucleotides. Where 210 and 211 are prepared by an enzymatic means, such as PCR, the lengths of 210 and 211 range from about 100 nucleotides to about 10,000 nucleotides. Highly preferred lengths of 210 and 211 prepared by enzymatic means fall within the range of about 200 to 350 nucleotides. When 210 and 211 are annealed together, they form a perfect duplex having a single-stranded terminus that represents the signaling acceptor domain-binding site (212). A 212 has sequence complementarity with element 208.

Referring to FIG. 4D, certain embodiments of structure 200 may be composed of fragment libraries of 201 and 202 having enzymatically-prepared nucleic acid sequences from source DNA for 203 and 205. For these embodiments, many non-productive 200 bipartite structures arise from annealing two noncontiguous 201 and 202 structures in the fragment libraries. It is preferable control the hybridization process such that 203 and 205 initially hybridize to contiguous sequences of 207 before 204 and 206 interact. For this reason, it is preferable to include oligonucleotides, or subsequences thereof, that are complementary to 204 and/or 206 (see, e.g., FIG. 4E, 204c and 206c) in the initial hybridization reaction that includes 201, 202 and 207. Once 203 and 205 have hybridized to 207, the sample is washed under appropriate stringency conditions to remove the unbound sequences (201, 202 and 204c and/or 206c). Thereafter, hybridization conditions are adjusted to permit annealing of 204 and 206 and formation of 208.

The sequences of 208 and 212, as well as other nucleic acids described herein having sequences with complementarity to 208 and 212, are specified by chemical design as either palindromic or non-palindromic sequences. Both types of structures for 208 and 212 are formed by controlling the chemical design of the termini. This control is accomplished either by selecting an appropriate synthetic oligonucleotide chemical sequence for creating the desired sequence termini or by choosing a suitable restriction enzyme that creates the desired product sequence termini, particularly for generating such termini from a doubled-stranded form of 209.

Palindromic sequence designs for 208 and 212 permit multiple copies of 200 and 209 to interact to form 200:200, 200:209, and 209:209 hybridization pairs. Preferred interactions include 200:209 and 209:209 hybridization pairs.

Non-palindromic sequence designs for 208 and 212 permit multiple copies of 200 and 209 to interact to form 200:209 combinations.

Because 209 has two 212, a 209 may be designed having one palindromic 212 and one non-palindromic 212. Such a design for 209 permits formation of 200:209 hybridization interactions when 200 is designed having a non-palindromic sequence for 208 that is complementary to a non-palindromic sequence of one 212 in 209.

A 209 includes at least one label. Preferably, 209 includes a plurality of labels. Such labels are incorporated internally or at the termini of 209. Preferably, 209 is labeled internally when 210 and 211 are produced by an enzymatic means, such as by PCR.

Figure 4E:
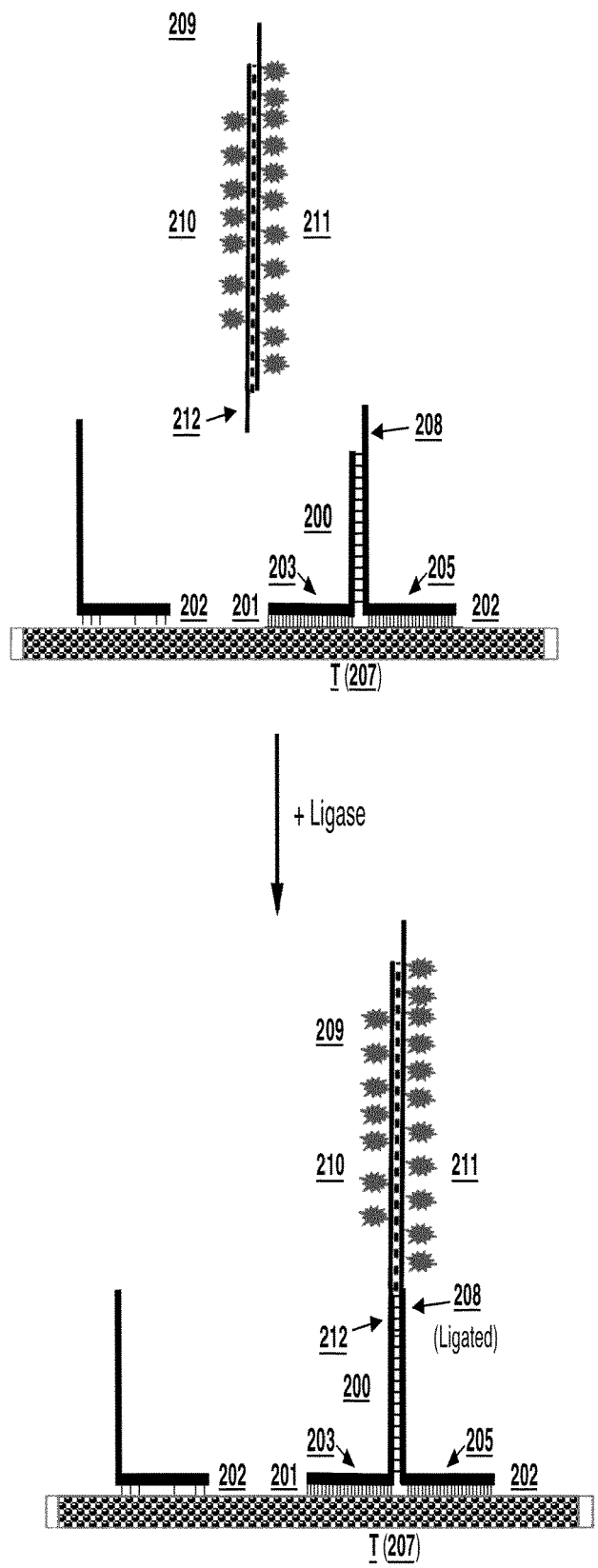

Referring to FIG. 4E, signal detection for a given nucleic acid target is achieved with 200 and 209 in the following manner. Nucleic acids 201, 202, 210 and 211 are contacted with a sample that includes nucleic acid target having element 207 to permit hybridization. Without being limited to any particular theory regarding order of reaction, the following illustrates the operative principle. A 207 serves as hybridization substrate for annealing 203 and 205. The formation of 200 via hybridization of 204 and 206 occurs either before or after 203 and 205 anneals to 207. Preferably, 210 and 211 hybridize to form 209. Once 209 is formed, 209 is available to form a hybrid with 200 via complementary base-pairing between 212 and 208. Ligation buffer containing ligase is added to the sample to permit ligation of 208 to 212, resulting in a covalent conjugate forming between 200 and 209. Following ligation, the sample is washed to remove any non-hybridized 201, 202, 210 and 211 and any non-conjugated 209. The detection of 207 is achieved with the signaling label located in 209.

Various permutations and modifications of the foregoing signal detection method will be apparent to one skilled in the art based upon this disclosure and fall within the scope of the present invention. For example, it may be preferable to pre-form certain embodiments of 200 before contacting a sample containing 207. Likewise, 209 can be pre-formed before contacting the sample. Similarly, the order of addition of 200 and 209 to a sample containing 207 can be configured to permit inclusion of additional wash steps. For example, any unbound 200 from the contacted sample mixture can be removed using washes prior to adding 209 to the contacted sample mixture.

Figure 5:
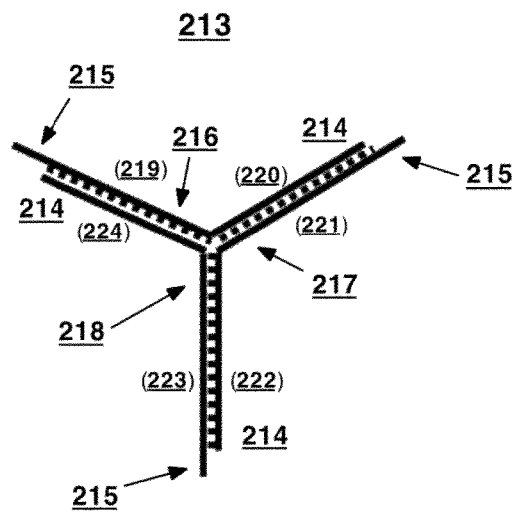
FIG. 5A illustrates a signal amplification adaptor 213 and its oligonucleotide components, 216, 217 and 218.
FIG. 5B illustrates the principle of operation of signal adaptor 213, wherein the signal amplification adaptor 213 can form alternative complexes between 200 and 209.
FIG. 5C illustrates the principle of operation of signal adaptor 213, wherein signal amplification adaptor 213 can form alternative complexes between 200 and 209.
Figure 5:
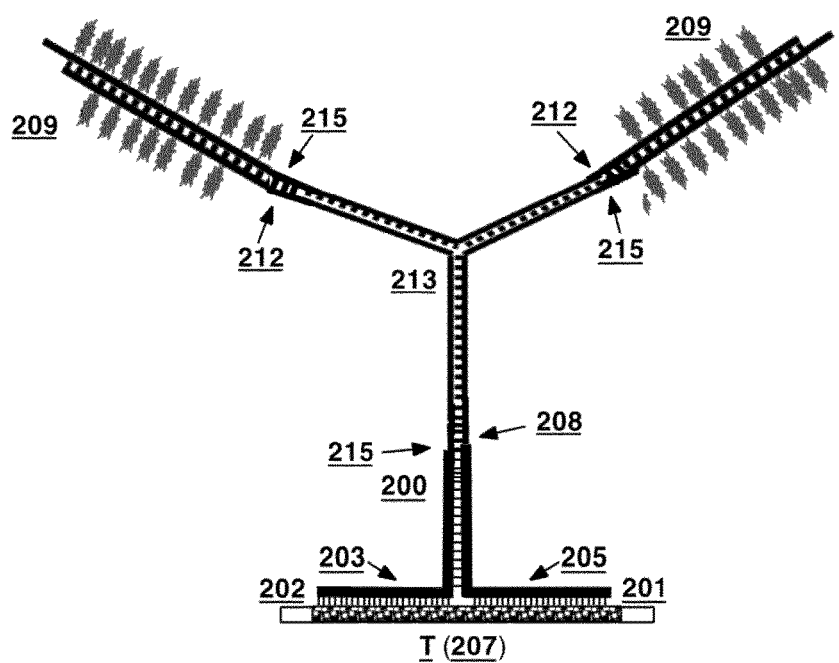
Figure 5:
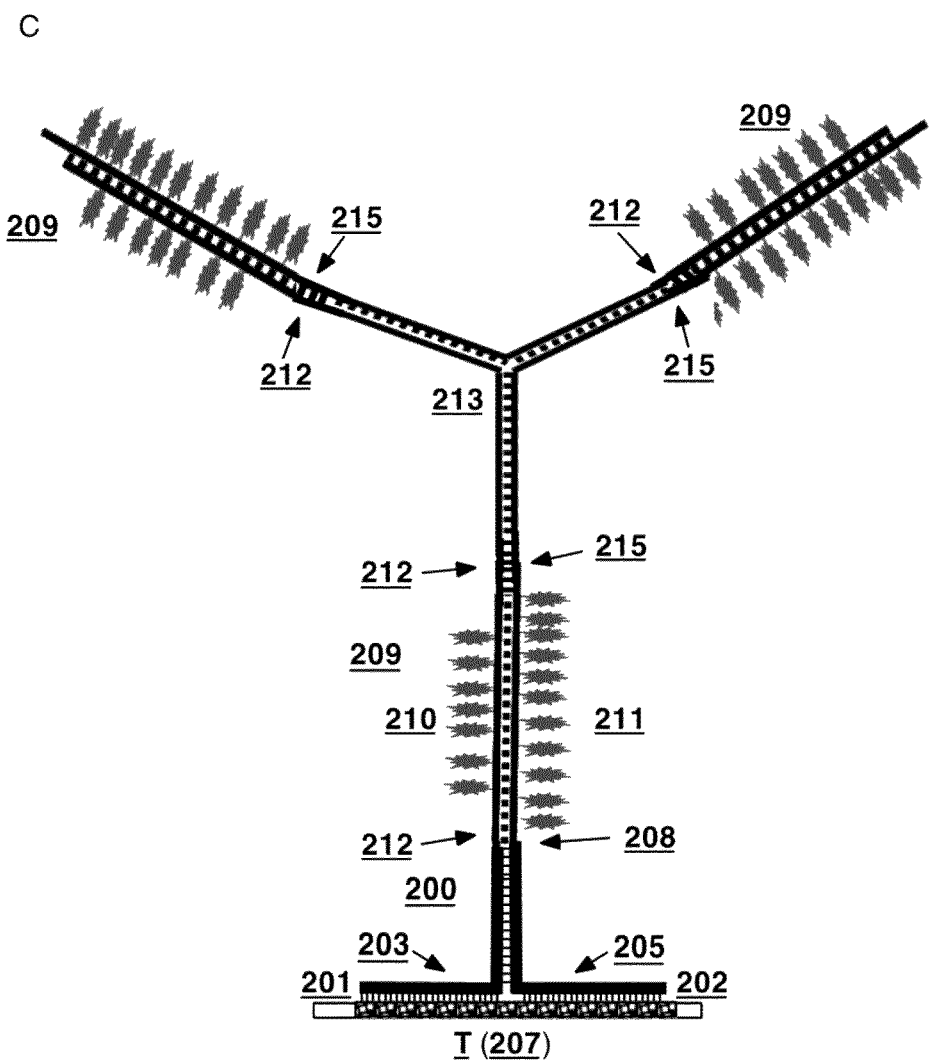

Referring to FIG. 5, signal amplification is accomplished using adaptor molecule 213. A 213 contains a plurality of signal acceptor domains (214), wherein each signal acceptor domain includes a signal domain hybridizing site (215). A 215 is complementary to 212 and/or 208.

Like 208 and 212, the sequence of 215 may be palindromic or non-palindromic. Because it is preferable to use synthetic oligonucleotide chemistry to produce 216, 217 and 218, the sequence design of 215 is precisely determined. Accordingly, the design of 215 will follow the same considerations as described for 208 and 212.

A plurality of 214 for 213 refers to at least 3 copies of 214. A plurality of 214 for 213 has preferable range from 3-6. Most preferably, 3 copies of 214 are present in 213.

An example of 213 having 3 copies of 214 is illustrated in FIG. 5A. To form 213 having this structure, three pairwise complementary single-stranded nucleic acids, 216, 217 and 218 are required. A 216 includes 219 and 220; a 217 includes 221 and 222; and a 218 includes 223 and 224.

The nucleic acids 216, 217 and 218 can have a length from about 30 nucleotides to about 120 nucleotides. Preferred lengths of 216, 217 and 218 range from about 50 nucleotides to about 90 nucleotides. The preferred lengths of the corresponding portions of 216, 217 and 218, namely 219 through 224, are about one-half the respective lengths of 216, 217 and 218. As explained above, such molecules are preferably made by using synthetic oligonucleotide chemistries.

As for the sequence composition of 216, 217 and 218, it is preferable to have the identical single-stranded sequence for each resultant 215 present at the terminus of each 214. This is due to the fact that 215 hybridizes to 212 during nucleic acid hybridization probe assay conditions. For 209 structures having identical 215 motifs that are complementary to a non-palindromic 212 in a 209, formation of $200:209:213:(209)_2$ hybridization complexes result. Where 215 hybridizes to 208 as well as 212, it may be preferable to have at least one of the 215 have complementarity to 208. Such a design permits formation of $200:213:(209)_2$ complexes (see, for example, FIG. 5B). Where 208, 212, and 215 share a common palindromic complementary sequence, multiple types of complexes result, including $200:213:(209)_2:[213:(209)_2]_n$ where n is any integer greater than 1 (see, for example, FIG. 5B) and $200:209:213:(209)_2:[213:(209)_2]_n$ where n is any integer greater than 1 (see, for example, FIG. 5C), among others.

Without being limited to any particular theory regarding order of reaction, the following illustrates the assembly principle for 213. The nucleic acids 216, 217 and 218 form 213 by 219 hybridizing to 224; 220 hybridizing to 221; and 222 hybridizing to 223.

Higher order structures having a plurality of 213 monomers can be formed. Such structures arise where at least one 214 fails to form for a given 213 monomer. The unpaired nucleic acids of one incomplete 213 assembly act as pairing partners with the unpaired nucleic acids of similarly incomplete 213 assemblies.

Because such higher order assemblies can lead to precipitation rather than productive reaction in nucleic acid hybridization probe assays, it is desirable to preform 213 as discrete unimolecular assemblies (213 monomers) and purify them prior to use in assays. Any suitable means of purifying 213 monomers may be used, such as size exclusion gel chromatography.

Labeling Considerations

As used herein, "label" refers to any moiety that can generate a detectable signal based upon the inherent chemical property of the moiety or its ability to react with another molecule. Examples of labels include radioactive, fluorescent, or chemiluminescent molecules or an enzyme. Labels also include molecules having affinity for other molecules that are readily detectable, such as biotin-avidin systems, and antigen-antibody systems.

Preferred chemiluminescent labels include acridinium compounds. Exemplary acridinium compounds include acridinium-9-carboxamides and acridinium-9-carboxylate aryl esters. Such compounds are described, for example, in U.S. Pat. No. 5,783,699 to Mattingly et al., entitled CHEMILUMINESCENT ACRIDINIUM SALTS and U.S. Patent Publication US20100015655A1 to Adamczyk et al., entitled METHODS AND KITS FOR DETECTING AND QUANTIFYING DAMAGE CAUSED BY A PARASITE, the contents of which are hereby incorporated by reference in their entirety.

For FISH detection systems, chromosomal probes typically are directly labeled with a fluorophore, an organic molecule that fluoresces after absorbing light of lower wavelength/higher energy. The fluorophore allows the probe to be visualized without a secondary detection molecule. After covalently attaching a fluorophore to a nucleotide, the nucleotide can be directly incorporated into the probe with standard techniques such as nick translation, random priming, and PCR labeling. Alternatively, deoxycytidine nucleotides within the probe can be transaminated with a linker. The fluorophore then is covalently attached to the transaminated deoxycytidine nucleotides. See, for example, U.S. Pat. No. 5,491,224 to Bittner et al., entitled DIRECT LABEL TRANSAMINATED DNA PROBE COMPOSITIONS FOR CHROMOSOME IDENTIFICATION AND METHODS FOR THEIR MANUFACTURE, the contents of which are hereby incorporated by reference in its entirety.

For example, fluorophores of different colors are chosen such that each chromosomal probe in the set can be distinctly visualized. For example, a combination of the following fluorophores may be used: 7-amino-4-methylcoumarin-3-acetic acid (AMCA), Texas Red™ (Molecular Probes, Inc., Eugene, Oreg.), 5-(and-6)-carboxy-X-rhodamine, lissamine rhodamine B, 5-(and-6)-carboxyfluorescein, fluorescein-5-isothiocyanate (FITC), 7-diethylaminocoumarin-3-carboxylic acid, tetramethylrhodamine-5-(and-6)-isothiocyanate, 5-(and-6)-carboxytetramethylrhodamine, 7-hydroxycoumarin-3-carboxylic acid, 6-[fluorescein 5-(and-6)-carboxamido] hexanoic acid, N-(4,4-difluoro-5,7-dimethyl-4-bora-3a,4a diaza-3-indacenepropionic acid, eosin-5-isothiocyanate, erythrosin-5-isothiocyanate, and Cascade™ blue acetylazide (Molecular Probes, Inc., Eugene, Oreg.).

Other molecules having fluorescent properties are also suitable labels. For example, a protein like phycoerythrin, a 240 kDal protein, displays robust fluorescent properties. A single-stranded oligonucleotide can be conjugated to the protein to serve as a signaling agent (e.g., a labeled form of 107 or 110, see, for example FIG. 2). Other labels having fluorescent properties may also be used, including quantum dots, nanocrystals and related semiconductor fluorophores.

For embodiments of nucleic acid probes that include a plurality of labels, the labels selected for inclusion may include one single type of label or multiple types of labels. Where multiple types of labels are include within nucleic acid probes having a plurality of labels, one can use as many as from 2 to 20 different types of labels. In these instances, the plurality of labels can have different optical or spectroscopic properties that enable one to visualize, discern or quantify as many as from 2 to 20 different hybridization events (for example, one or more genetic loci in a FISH application). In highly preferred embodiments, a plurality of labels ranging from 2 to 5 different labels having discrete, differentiable optical or spectroscopic properties can be used in nucleic acid probes. For embodiments of nucleic acid probes that include plurality of labels, multiplexing analysis of the resultant complex hybridization signals can be assessed with microscope filters of specified spectral characteristics (bandpass), or deconvoluted following imaging and processing of the image with appropriate software. Such imaging software applications are commonly available in the art.

Fluorescent probes are visualized with a fluorescence microscope and an appropriate filter for each fluorophore, or by using dual or triple band-pass filter sets to observe multiple fluorophores. See, for example, U.S. Pat. No. 5,776,688. Alternatively, techniques such as flow cytometry can be used to examine the hybridization pattern of the chromosomal probes.

Probes also can be indirectly labeled with biotin or digoxygenin, or labeled with radioactive isotopes such as $^{32}P$ and $^{3}H$, although secondary detection molecules or further processing then is required to visualize the probes. For example, a probe indirectly labeled with biotin can be detected by avidin conjugated to a detectable marker. For example, avidin can be conjugated to an enzymatic marker such as alkaline phosphatase or horseradish peroxidase. Enzymatic markers can be detected in standard colorimetric reactions using a substrate and/or a catalyst for the enzyme. Catalysts for alkaline phosphatase include 5-bromo-4-chloro-3-indolylphosphate and nitro blue tetrazolium. Diaminobenzoate can be used as a catalyst for horseradish peroxidase.

Fluorescent labels are visualized by any suitable means of detecting fluorescence. Preferably, the labels are visualized with fluorescence microscopy and appropriate filters. Such techniques and automated digital imaging systems are well known in the art.

The labeling procedures described for labeling structure 100 also apply to other probes, such as 107, 110, 112, 113 and 209.

Probe Preparation

Figure 6:
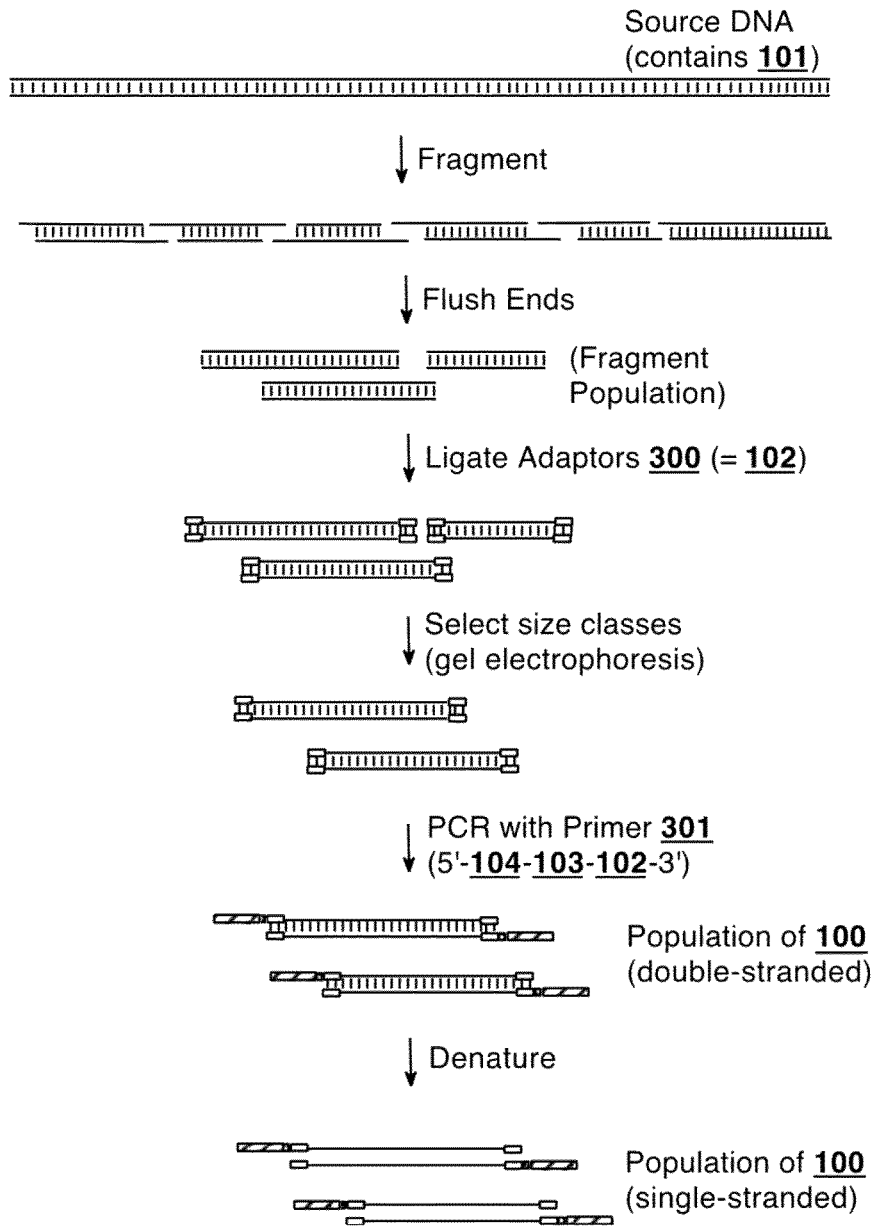
FIG. 6 illustrates a method for producing nucleic acid hybridization probes of structure 100.

In certain embodiments, structure 100 having elements 101, 102, 103 and 104 is prepared in the following manner (see FIG. 6). A nucleic acid sample that includes the sequence of element 101 is fragmented. Any means of fragmenting nucleic acids known in the art can be used. Preferred means of fragmenting nucleic acids includes sonication and restriction enzyme digestion. Sonication is the most preferred means for fragmenting nucleic acids. The sonication procedure is performed on the nucleic acid sample to achieve a population of nucleic acid fragments having a length from about 50 nucleotides to about 5,000 nucleotides. Preferred lengths of the nucleic acid fragments range from about 150 nucleotides to about 500 nucleotides. Highly preferred lengths of nucleic acid fragments range from about 200 nucleotides to about 350 nucleotides.

The population of nucleic acid fragments will typically have unflushed termini following sonication. The termini are flushed using enzymes having polymerase and/or exonuclease activities specific for single-stranded substrates. Such enzymes and procedures are well known in the art.

Adaptors (300) having the sequence of element 102 and its complement are ligated onto the flushed termini of the population of nucleic acid fragments to generate a population of nucleic acid fragments bearing terminal adaptors. Optionally, however, Adaptors (300) having a single-base overhang (e.g., T-overhang) to ligate onto a complementary base overhang (e.g., an A-overhang) containing termini of the population of nucleic acid fragments can also be used to generate a population of nucleic acid fragments bearing terminal adaptors. Though one double-stranded adaptor sequence is sufficient for this purpose, it is preferable to use two double-stranded adaptors that differ in sequence composition. The adaptors can be used as 5'-phosphorylated molecules, though it is preferable to use non-5'-phosphorylated molecules. The ligation reaction is catalyzed with any suitable ligase known in the art. It is also desirable that the two strands of each adaptor differ in their lengths so that only one adaptor terminus is compatible for ligating to the flushed termini of the DNA fragments without generating terminal concateners of adaptors at the termini.

The purpose of the adaptors is to serve as primer binding sites for an oligonucleotide primer (301) in a polymerase chain reaction (PCR). The design of 301 has the sequence (5' to 3') composition of 104, 103 and 102. Thus, 102 that is present in 301 hybridizes to 300 of each member of the population of nucleic acid fragments and serve as a primer for polymerase-mediated extension reaction during PCR. After the first cycle of PCR, all amplified products representative of the population of fragmented nucleic acids contain a 5'-3' terminal structure having 104, 103 and 102. Because 103 includes a moiety that blocks polymerase extension or elongation at the site on the strand complementary to 103, the resultant double-stranded PCR products after the second cycle of PCR have single-stranded, 5'-termini comprising 104.

Once adaptors 300 are ligated onto the termini of the population of nucleic acid fragments, the mixture is fractionated according to size. Size-fractionation methods include use of gel electrophoresis, differential polyethylene glycol (PEG) precipitation or chromatographic sizing (e.g., HPLC). In the case of size-fractionation by gel electrophoresis, the gel fractions representing the population of nucleic acid fragments in the preferred range of 200 bp to 350 bp are excised from the gel. The gel slices containing the population of nucleic acid fragments is heated briefly to melt the gel matrix and an aliquot of the mixture is removed for PCR with the appropriate single-strand versions of 301 as primers.

Optionally, preparative PCR of the population of nucleic acid fragments containing adaptors 300 can be performed prior to gel electrophoresis. Preparative PCR would be accomplished using the appropriate single-strand versions of 300 as primers.

In certain embodiments, structure 100 will contain labeled cytosines in element 104. In preparing structure 100 of this type, it is preferable to incorporate the label into all cytosines of 104 before beginning PCR. For this reason, it is preferable to not to use cytosines in the primer design of the sequence of 102 for elements 300 and 301. The reason for this design decision is that exhaustive labeling of all cytosines of 301 would be localized to only 104, thereby leaving the primer portion of 301, namely 102, unchanged. Because 301 hybridizes to 300 by virtue of both 300 and 301 containing the identical 102 (and its complement), these cytosine sequence requirements also apply to the design of element 300 corresponding to the primer sequence strand.

The foregoing sequence constraints on the structure of element 102 can be relaxed or need not apply in the following circumstances: (a) where one incorporates labels into 104 during the chemical synthesis of 301; or (b) where one does not use labeled 301 for preparing structure 100. In the case where structure 100 is prepared using unlabeled 301, structure 100 can be post-labeled following its preparation.

Where 104 is post-labeled using bisulfite to aminate the nucleobases, it is preferable to use a non-denatured, double-stranded form of structure 100 so that the single-stranded 5'-termini containing 104 are preferentially aminated. Because 102 of structure 100 is double-stranded, any cytosines present in 102 would not be subject to the same degree of amination as would be the case for 102 found in the single-stranded form of 301.

Where structure 100 is post-labeled, for example, by using bisulfite procedures to aminate the nucleobases throughout 100, it is preferable to use a denatured, single-stranded form of structure 100 so that the entire molecule is available for chemical modification. A post-labeling procedure results in an increase of label content throughout structure 100. In the case of using a base-specific modification reagent, however, it is preferable to omit the chemically susceptible base(s) from 104, particularly for embodiments of structure 100 in which 104 serves as a binding site for another nucleic acid (e.g., a 107; see FIG. 1C or 2). For example, a post-labeling procedure using bisusfite to modify cytosines within structure 100 is preferably done using as substrate structure 100 having cytosines omitted from 104.

Where structure 100 is used as an indirectly-labeled probe, 104 is not labeled and only serves as a binding site for at least one other nucleic acid that is labeled. For structure 100 used for these indirect labeling applications, the sequence of 102 can also include any sequence composition, including cytosines.

Most nucleic acids that are substrates for preparing structure 100 are cloned molecules found in DNA vectors (e.g., plasmid, phagemid, BAC, YAC, etc.). For most FISH applications, purifying the desired nucleic acids from the vector sequences is not required before preparing structure 100, because the vector sequences would not hybridize to the nucleic acid targets. There are instances for other nucleic acid detection systems where the vector sequences interfere with identifying positive signals (or contribute to non-specific hybridization backgrounds) if such sequences were included in the mixture used for preparing structure 100. And even for certain FISH applications, where it is desirable to detect only part of a gene in a chromosome, it may be important to prepare a subset of nucleic acid substrates corresponding to that part of the gene from a source (i.e., a vector) that contains the entire gene. Yet in other cases, the desired nucleic acid sequences may be available only as whole genomic DNA as opposed to cloned molecules. In each of these cases, to the extent that the desired nucleic acid sequences are known, preparative PCR may be performed with suitable DNA and primers to amplify the desired nucleic acid sequences. Once obtained, these sequences can be isolated or purified for use as substrates for preparing structure 100 according to the methods outlined above.

In some hybridization applications, such as FISH, it can be important to further refine the target sequences to exclude certain repetitive sequence elements found ubiquitously in natural sequences. In this regard, one can select a priori the precise boundaries and composition of the desired target sequences by virtue of PCR primer design that specifies the PCR products to be generated. For example, one can analyze a genetic locus or plurality of genetic loci from a given chromosomal region of interest to delineate non-repetitive genetic information (for example, gene-coding information) from repetitive sequence elements found dispersed throughout all chromosomal DNA (for example, SINEs, LINEs, and LTRs). Once delineated, one can then design PCR primers that can be used to amplify only the non-repetitive genetic information (that is, sequences lacking repetitive sequence elements as defined above) as the preferred target sequences. In many cases, the preferred target sequences can range in size from about 100 bp about 6 kbp. Such non-repetitive sequence material is preferred for use in FISH applications, because the resultant probes generated from non-repetitive sequence element DNA obviates or at least substantially reduces the need to include $C_o t-1$ DNA in FISH applications, the latter of which reduces signal intensity and robustness. Once obtained, these non-repetitive sequences can be isolated or purified for use as substrates for preparing structure 100 according to the methods outlined above.

For nucleic acid substrates having a size that that falls with the preferred range of 100 bp to 500 bp, the sonication step can be omitted. For these embodiments, structure 100 may be amplified directly from suitable nucleic acid substrates using as primers modified forms of 301. Because 300 need not be ligated onto the termini of such nucleic acid substrates, the structure of 301 does not contain 102 in the form of an artificial sequence. In this case, the artificial sequence of 102 is replaced by a suitable sequence that hybridizes to the natural sequence of the nucleic acid substrate. Such suitable primer sequences define and include the boundaries of the 101 for structure 100 generated during PCR. In certain instances, it is advantageous to perform preparative PCR with primers containing only 102 sequences for amplifying the desired nucleic acid substrate before performing PCR with primers containing 301 sequences for generating structure 100.

Figure 7:
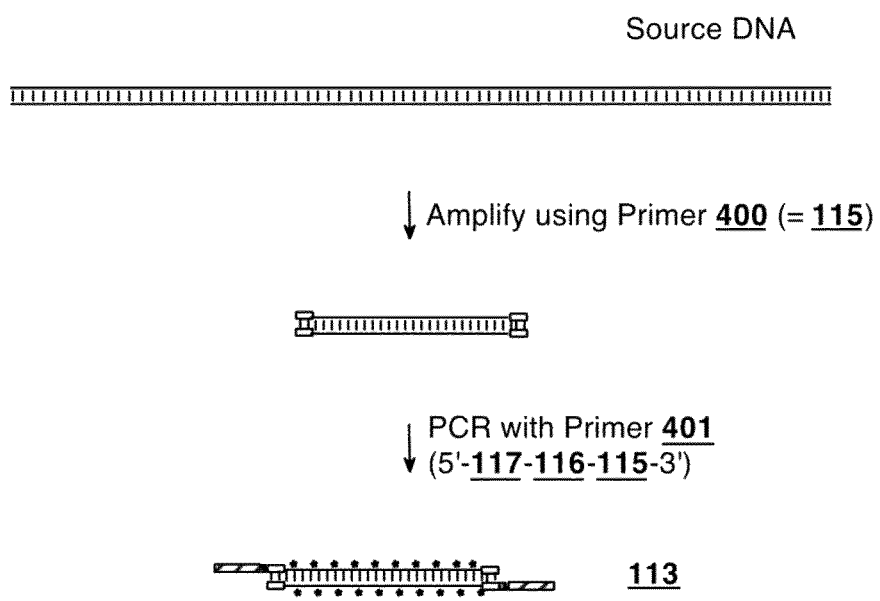
FIG. 7 illustrates a method for producing nucleic acid hybridization probes of structure 113. Asterisks indicate internal labels incorporated during DNA amplification.

Structure 113 is prepared according to the same procedures described previously for structure 100, except for the following modifications in substrate choice, primer selection and the design of the PCR-mediated construction of structure 113. For 113, it is preferable to use a single source DNA without fragmentation. Referring to FIG. 7, source DNA containing primers (400) at the termini is prepared. A 400 includes a 3' region having a sequence that is complementary to and primes DNA synthesis from a site within the nucleic acid sequence target. Preferably, 400 can include a 5' region having additional sequences unrelated the nucleic acid sequence target (15). An oligonucleotide primer 401 having the sequence (5' to '3) composition 117, 116 and 115 is prepared using chemical synthesis methods. The target sequence is initially obtained by DNA amplification using a set of primers consisting of 400, where each primer 400 is specific for a sequence defining the boundaries of the desired target sequence. Structure 113 can be prepared from DNA containing terminal sequences 400 using PCR with primer 401.

Labeled 113 can be prepared in a variety of ways. In one embodiment, 113 is labeled during DNA amplification using a nucleotide triphosphate cocktail that contains a modified nucleotide (e.g., aminoallyl dUTP) that can be labeled with a fluorophore (e.g., using an activate ester form of a fluorophore; the internal labels are not illustrated in FIG. 7). Alternatively, 113 can be prepared, for example, by using cytosine-specific labeling techniques. In such embodiments, 401 having cytosines located in only 117 are used, wherein the cytosine content of 117 is labeled, for example, by using bisulfate/amination/fluorophore conjugation procedures described above. Alternatively, 113 can be post-labeled throughout the entire molecule using a suitable chemical modification post-labeling procedure. As explained above for certain embodiments of 101 prepared in this fashion, it is preferable to omit chemically-susceptible bases from 117 in structure 113.

Preferably, 209 is prepared with at least one internal label using any technique known in the art. The label is preferably incorporated into 209 by PCR amplification of a longer source DNA using primers and a dNTP cocktail that includes a modified nucleotide (e.g., aminoallyl dUTP). Following preparation of the amplified DNA containing the modified nucleotide, the DNA is digested with suitable restriction endonuclease that generates products having the structure of element 212. Such restriction sites can be designed into the primers used to amplify the source DNA. Alternatively, such restriction sites may exist within the original source DNA. Once the amplified DNA is subjected to digestion with the appropriate restriction enzyme, suitable size classes for 209 can be gel-purified and conjugated to a suitable label (e.g., using an activated ester of a fluorophore).

Because 201, 202, 216, 217 and 218 are typically less than 200 nucleotides in length, it is preferable to prepare these molecules using synthetic oligonucleotide chemistry procedures.

In certain embodiments, however, 201 and 202 include segments of nucleic acid sequences for 203 and 205, respectively, wherein the lengths of 203 and 205 can be considerably longer than 200 nucleotides in length. Such embodiments of 201 and 202 are prepared with standard molecular biology methods using a combination of synthetic oligonucleotide chemistry and nucleic acid sequence target DNA as source DNA.

Figure 8:
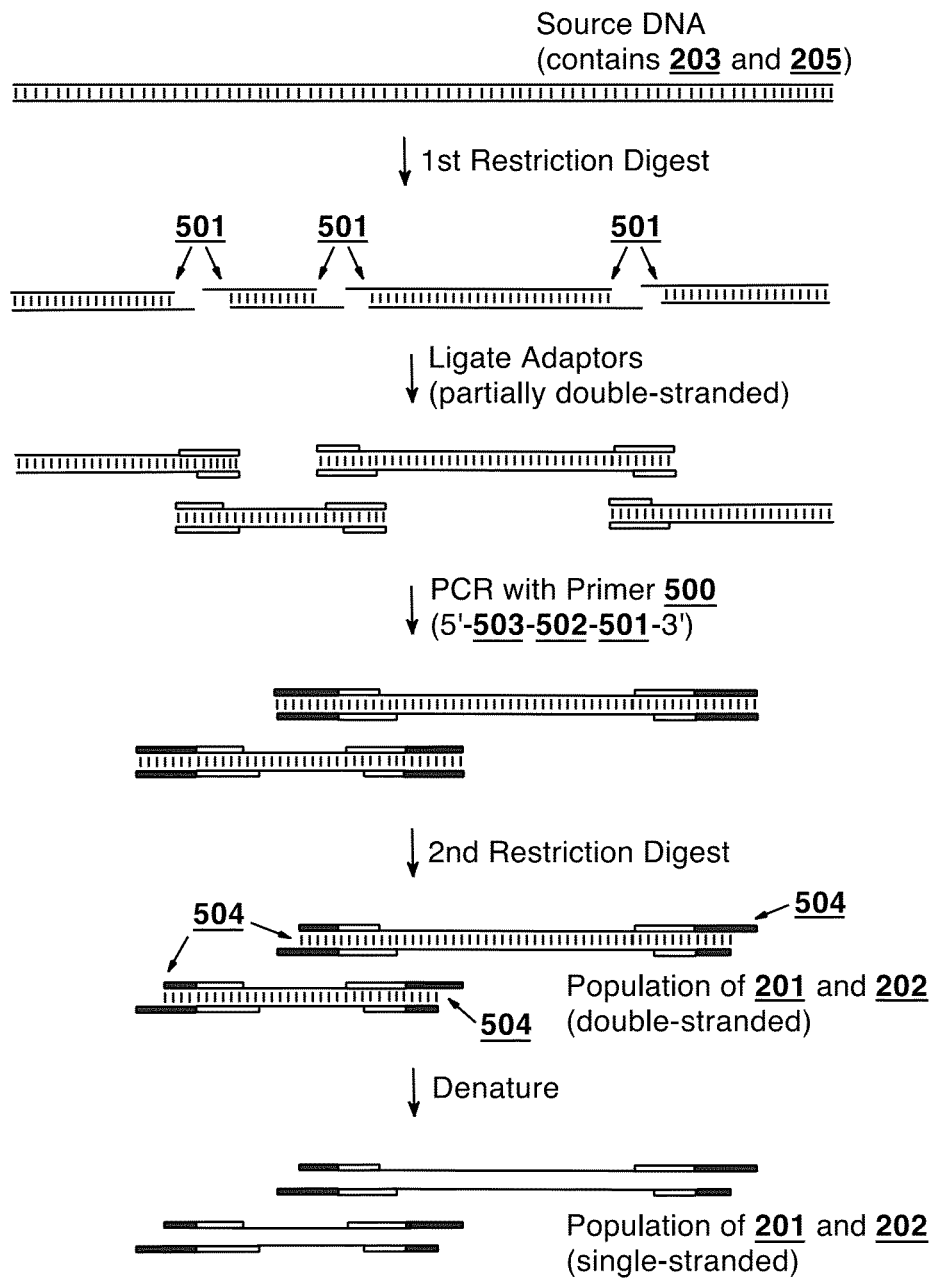
FIG. 8 illustrates a method for producing nucleic acid hybridization probes of structure 200 (i.e., 201 and 202).

Referring to FIG. 8, source DNA containing 203 and 205 candidate sequences is digested with a first restriction endonuclease to form a plurality of restriction fragments having defined termini (501). Such 501 may be flush-ended or contain single-stranded termini. The resultant restriction fragments are ligated to adaptors having appropriate terminal sequences compatible with ligation. Where the first restriction endonuclease generates products having a single-stranded terminus 501, it is appropriate to use a partially double-stranded adaptor having as a first strand (500) the sequence (5'→3') composition, 503, 502 and 501, and as a second strand the complementary strand such that 501 is a single-stranded and 502 and 503 are double-stranded. Where the first restriction endonuclease generates products having a flush-ended 501 structure, a fully double-stranded adaptor composed of 503, 502 and 501 is appropriate.

Optionally, where the first restriction endonuclease generates products having a single-stranded terminus 501, such products may be flush-ended using appropriate enzymes. The resultant flush-ended terminal products are suitable for ligation to flushed-ended adaptors composed of a fully double-stranded adaptor composed of 503, 502 and 501.

The structure 502 corresponds to a sequence that serves two purposes. First, 502 is an extension sequence for binding to part of a primer (500) for promoting DNA amplification of the restriction fragment population (FIG. 8). Second, 502 (and its complement) acts as the equivalent of 204 and 206 when 501 is ligated to both ends of each member of the restriction fragment population of nucleic acid sequence targets (i.e., the candidate sequence equivalents of 203 and 205).

The structure 503 includes a substrate for a second restriction enzyme having certain preferred substrate recognition sequence criteria. First, 503 corresponds to a substrate for a restriction enzyme that does not recognize the same substrate sequence or subsequence of the first restriction enzyme. Second, 503 is cleaved by the second restriction enzyme to generate a single-stranded product terminus (504) having preferably 1-6 nucleotides and more preferably at least 3 nucleotides. Preferably, the second restriction endonuclease has a recognition sequence that is sufficiently long so as to cleave infrequently (e.g., less than once every 4,000 nucleotides). Optionally, 503 may be 5' end-labeled or prepared with an internal label 5' to the second restriction enzyme cleavage site corresponding to the restriction enzyme product sequence at one terminus. Preferred labels are fluorescent or chemiluminescent.

The resultant adaptor-containing restriction fragment population is subjected to DNA amplification using the single-stranded primer 500 corresponding to the sequence: (5') 503-502-501 (3'). Optionally, 500 can be 5' end-labeled. Following amplification of the fragment population to generate amplified products, the population of amplified products is digested with the second restriction enzyme to release any attached 5'-label and to generate the single-stranded terminus 504. The cleaved products can be subjected to further purification or used immediately as embodiments of 201 and 202 following denaturation of the double-stranded fragment population.

The single-stranded terminus 504 becomes a signaling domain acceptor-binding site 208 upon formation of the duplex between a 502 and its complement (i.e., the equivalent of 204 and 206). Thus, 504 can form 208 when 203 and 205 bind to a 207 composed of the contiguous sequence complement of 203 and 205.

Nucleic Acid Hybridization Probe Applications

The described nucleic acid hybridization probes have broad utility for use in all forms of nucleic acid detection that is achieved by use of nucleic acid hybridization probes. The nucleic acid hybridization probes can be used for detecting nucleic acid sequence targets in solution or bound to immobilized supports. Examples of applications where the composition and methods can be used to detect nucleic acid sequence targets in solution include PCR, real-time PCR, quantitative PCR, PNA clamp-mediated PCR and digital PCR. Examples of applications where the compositions and methods can be used to detect nucleic acid sequence targets immobilized to solid supports include northern blots, southern blots, dot blots, slot blots, microarrays, particle-based assays and FISH assays. Such applications are amenable to numerous fields, including medical diagnostics, molecular medicine, forensic science, specimen and organism cataloging and microbial pathogen epidemiology. A detailed description of the utility of the nucleic acid hybridization probes is presented below for FISH applications.

The superior sensitivity of the nucleic acid hybridization probes described herein is suitable for detecting and monitoring of cancers associated with amplification, deletion, rearrangement or translocation of chromosomal material. The application of the methods and compositions provides an effective means to monitor treatment efficacy directed to cancer therapeutic targets. For example, the method enables the physician to diagnose the therapeutic outcome for treating a patient having a cancer with an anti-cancer therapeutic agent, particularly for cancers that are predisposed to developing resistance to anti-cancer therapeutic agents. The method enables a physician to confirm the presence of specific chromosomal anomalies in cancer cells, thereby permitting the physician to develop an alternative treatment strategy as warranted. The methods and compositions also enable one to survey for tumor recurrence/progression in patients with particular gene-specific or chromosomal region-associated cancers. Further, the methods and compositions enable one to provide reliable prognoses of cancers, which directly provide guidance to the treating physician of definitive treatments having the greatest benefit to the patient.

Cancers are associated with a number of chromosomal aberrations (for example, amplification, translocation, deletion, or rearrangement of specific nucleic acid sequence target in one or more chromosomes). To the extent that such aberrations are detectable for certain cancers, one can use the nucleic acid probes of the invention to detect, diagnose provide prognosis, screen, or otherwise detect those cancers by hybridizing a set of chromosomal probes to the samples, wherein the set includes probes specific for a type of cancer associated with amplification, translocation, deletion, or rearrangement of specific nucleic acid sequence target in one or more chromosomes.

Relevant cancers amenable for use with the present nucleic acid probe technology include, but are not limited to prostate cancer, adrenocortical cancer, biliary cancer, breast cancer, ovarian cancer, endometrial (uterine) cancer, cervical cancer, colorectal cancer, esophageal cancer, gall bladder cancer, gastric cancer, glioma, glioblastoma, head and neck cancer, lung cancer, bladder cancer, pancreatic cancer, gastric cancer, and salivary gland cancer. Relevant samples amenable for use with the present nucleic acid probe technology include, but are not limited to urine, blood, cerebrospinal fluid, pleural fluid, sputum, peritoneal fluid, bladder washing, secretion, oral washing, tissue sample, touch prep and fine-needle aspirate.

Relevant chromosomal probes amenable for use in the present nucleic acid probe technology include, but are not limited to chromosome-specific markers, such as chromosome enumeration probes (CEPs), centromere-specific probes, telomere-specific probes, and genetic allele-specific probes. With respect to genetic allele-specific probes, genetic alleles defined by deletion, duplication, rearrangement, amplification, and the like, are within the scope of the present invention. Likewise, any genetic locus having a biological, correlative marker useful in the screening, diagnosis, prognosis or treatment of cancer (broadly defined as "cancer diagnostics") falls within the scope of the present invention. Examples of genetic loci having applications in cancer diagnostics include EGFRv3, CDKN2A/p16 (9p21) and p53 (17p13.1), among others.

For a typical FISH application, the following represents a typical procedure. Cells of a specimen are harvested, washed and pelleted. The cells of the pellet are usually washed in phosphate-buffered saline (PBS). The cells are suspended in PBS and re-collected by centrifugation. The cells can be fixed, for example, in acid alcohol solutions, acid acetone solutions, or aldehydes such as formaldehyde, paraformaldehyde, and glutaraldehyde. For example, a fixative containing methanol and glacial acetic acid in a 3:1 ratio, respectively, can be used as a fixative. A neutral buffered formalin solution also can be used, and includes approximately 1% to 10% of 37-40% formaldehyde in an aqueous solution of sodium phosphate. Slides containing the cells can be prepared by removing a majority of the fixative, leaving the concentrated cells suspended in only a portion of the solution.

The cell suspension is applied to slides such that the cells do not overlap on the slide. Cell density can be measured by a light or phase contrast microscope. For example, cells harvested from a 20 to 100 ml urine sample typically are suspended in a final volume of about 100 to 200 µl of fixative. Three volumes of this suspension (usually 3, 10, and 30 µl), are then dropped into 6 mm wells of a slide. The density of cells in these wells is then assessed with a phase contrast microscope. If the well containing the greatest volume of cell suspension does not have enough cells, the cell suspension is concentrated and placed in another well.

Prior to in situ hybridization, chromosomal probes and chromosomal DNA contained within the cell each are denatured. Denaturation process is performed in several ways. For example, denaturation can be effected with buffered solutions having elevated pH, with elevated temperatures (for example, temperatures from about 70° C. to about 95° C.), or with organic solvents such as formamide and tetraalkylammonium halides, or combinations thereof. For example, chromosomal DNA can be denatured by a combination of temperatures above 70° C. (for example, about 73° C.) and a denaturation buffer containing 70% formamide and 2×SSC (0.3M sodium chloride and 0.03 M sodium citrate). Denaturation conditions typically are established such that cell morphology is preserved. Chromosomal probes can be denatured by heat. For example, probes can be heated to about 73° C. for about five minutes.

After removal of denaturing chemicals or conditions, probes are annealed to the chromosomal DNA under hybridizing conditions. "Hybridizing conditions" are conditions that facilitate annealing between a probe and nucleic acid sequence target. Hybridization conditions vary, depending on the concentrations, base compositions, complexities, and lengths of the probes, as well as salt concentrations, temperatures, and length of incubation. The greater the concentration of probe, the greater the probability of forming a hybrid. For example, in situ hybridizations are typically performed in hybridization buffer containing 1-2×SSC, 50% formamide and blocking DNA (for example $C_o t-1$ DNA) to suppress non-specific hybridization. In general, hybridization conditions, as described above, include temperatures of about 25° C. to about 55° C., and incubation lengths of about 0.5 hours to about 96 hours. More particularly, hybridization can be performed at about 37° C. to about 40° C. for about 2 to about 16 hours.

Non-specific binding of chromosomal probes to DNA outside of the target region can be removed by a series of washes. Temperature and concentration of salt in each wash depend on the desired stringency. For example, for high stringency conditions, washes can be carried out at about 65° C. to about 80° C., using 0.2×SSC to about 2×SSC, and about 0.1% to about 1% of a non-ionic detergent such as Nonidet P-40 (NP40). Stringency can be lowered by decreasing the temperature of the washes or by increasing the concentration of salt in the washes.

Slides containing the samples are typically incubated in 2×SSC at 37° C. for 10-30 min. The slides are then incubated in 0.2 mg/ml pepsin at 37° C. for 20 min. Slides are subsequently washed twice in PBS at room temperature for 2 min. Cells are fixed in 2.5% Neutral Buffered Formalin at room temperature for 5 min. Slides are subsequently washed twice in PBS at room temperature for 2 min. The slides are subjected to dehydration by successive contact in solutions of 70%, 85%, and 100% ethanol at room temperature for 1 min. The slides are used immediately thereafter or stored at room temperature in the dark.

Hybridization can be performed with the HYBrite method or a conventional method. In the HYBrite method, a HYBrite™ system from Abbott Molecular (Downers Grove, Ill.) is used. Slides are placed on the HYBrite, and about 10 l of the probe set is added, covered, and sealed. The HYBrite is programmed as follows: 73° C. for 5 min, then 37° C. for 16 hr. Slides are then washed with 0.4×SSC (0.06 M sodium chloride/0.006 M sodium citrate)/0.3% NP-40 at 73° C. for 2 min., rinsed with 2×SSC/0.1% NP40 at room temperature for 2 min., and air dried. Slides are counter-stained with approximately 10 µl of DAPI II (125 ng/ml of 4,6-diamidino-2-phenylindole dihydrochloride).

In the conventional method (that is, Coplin jar method), a master mix containing chromosome probes is prepared in hybridization buffer containing 50% formamide, 2×SSC, 0.5 µg/ml Cot1 DNA, and 2 µg/ml HP DNA. The probe mix is denatured at 73° C. for 5 min., and slides are denatured in denaturation buffer (70% formamide, 2×SSC) in a Coplin jar at 73° C. for 5 min (6-8 slides/jar). Slides are rinsed in each of 70%, 85%, and 100% ethanol for 1 minute. Approximately 10 µl of hybridization mix are applied to each slide, covered with a cover slip, and sealed with rubber cement. Hybridization is performed in a humidified chamber at 37° C. overnight. Slides will be washed in 0.4×SSC/0.3% NP-40 at 73° C. for 2 min., then rinsed briefly in 2×SSC/0.1% NP-40 at room temperature. After the slides are air-dried, slides are counter-stained with DAPI II. Samples are enumerated by recording the number of FISH signals in 100 consecutive cells.

In a first aspect, a nucleic acid hybridization probe for detecting a nucleic acid target sequence is provided. The nucleic acid hybridization probe includes the following: a hybridization domain, an adaptor, a linker and a signaling domain. The hybridization domain includes a nucleic acid sequence having complementarity to the nucleic acid target sequence. The adaptor includes a nucleic acid sequence. The linker includes a moiety having at least one abasic site, such that the moiety blocks extension by an elongating polymerase on a nucleic acid template containing the moiety. The signaling domain includes a nucleic acid having at least one label or a nucleic acid having at least one nucleic acid domain for binding at least one additional nucleic acid.

According to a first embodiment of the first aspect, the linker includes at least one member selected from the group consisting of iSp1, iSp3, iSp9 and iSp18 or combinations thereof. According to a second embodiment of the first aspect, the linker includes iSp9 or iSp18. According to a third embodiment of the first aspect, the linker includes iSp9.

According to the first embodiment of the first aspect, the signaling domain further includes a plurality of labels. In one implementation of this embodiment, the plurality of labels includes a label spaced every 3-12 nucleotides. In another implementation of this embodiment, the plurality of labels includes a label spaced every 6 nucleotides. In another implementation of this embodiment, the plurality of labels includes two or more labels having discrete optical or spectroscopic properties.

According to a second embodiment of the first aspect, the at least one label includes a radioactive moiety, a fluorescent moiety, a chemiluminescent moiety, an enzyme, substrate for an enzyme, an antigen for an antibody, or a ligand for at least one ligand-binding molecule. According to a third embodiment of the first aspect, the at least one label includes a fluorescent moiety or a chemiluminescent moiety. According to a fourth embodiment of the first aspect, the at least one label includes a fluorescent moiety. According to a fifth embodiment of the first aspect, the hybridization domain includes a nucleic acid sequence lacking repetitive sequence elements.

According to another feature of the first embodiment of the first aspect, the at least one additional nucleic acid includes the following: another hybridization domain, another adaptor, another linker and a labeled nucleic acid. The another hybridization domain includes a nucleic acid sequence having complementarity to at least one nucleic acid sequence within the signaling domain. The another adaptor includes a nucleic acid sequence. The another linker includes a moiety having at least one abasic site, such that the moiety blocks extension by an elongating polymerase on a nucleic acid template containing the moiety.

According to the first embodiment of the first aspect, the signaling domain further includes a plurality of nucleic acid binding domains, wherein each nucleic acid binding domain is available for binding at least one additional nucleic acid. In a first implementation, the at least one additional nucleic acid includes the following: another hybridization domain, another adaptor, another linker and a labeled nucleic acid. The another hybridization domain includes a nucleic acid sequence having complementarity to at least one nucleic acid sequence within the signaling domain. The another adaptor includes a nucleic acid sequence. The another linker includes a moiety having at least one abasic site, such that the moiety blocks extension by an elongating polymerase on a nucleic acid template containing the moiety.

In a first aspect of the first implementation, the another linker includes at least one member selected from the group consisting of iSp1, iSp3, iSp9 and iSp18 or combinations thereof. In a second aspect of the first implementation, the another linker includes iSp9 or iSp18. In a third aspect of the first implementation, the another linker includes iSp9.

In the first aspect of the first implementation, the labeled nucleic acid includes a nucleic acid having a plurality of labels. In the first aspect of the first implementation, the labeled nucleic acid includes a double-stranded molecule having a plurality of labels. In the first aspect of the first implementation, the plurality of labels includes a label spaced every 3-12 nucleotides.

In the foregoing first aspect of the first implementation, wherein the labeled nucleic acid includes a nucleic acid having a plurality of labels, several additional features of the plurality of labels can be included. In one embodiment, the plurality of labels includes a label spaced every 6 nucleotides. In another embodiment, the plurality of labels includes two or more labels having discrete optical or spectroscopic properties. In yet another embodiment, the plurality of labels includes a radioactive moiety, a fluorescent moiety, a chemiluminescent moiety, an enzyme, substrate for an enzyme, an antigen for an antibody, or a ligand for at least one ligand-binding molecule. In yet another embodiment, the plurality of labels includes a fluorescent moiety or a chemiluminescent moiety. In yet another embodiment, the plurality of labels includes a fluorescent moiety.

In a first aspect, a nucleic acid hybridization probe for detecting a nucleic acid target sequence is provided. The nucleic acid hybridization probe includes the following: a hybridization domain, an adaptor, a linker and a signaling domain. The hybridization domain includes a nucleic acid sequence having complementarity to the nucleic acid target sequence. The adaptor includes a nucleic acid sequence. The linker includes a moiety having at least one abasic site, such that the moiety blocks extension by an elongating polymerase on a nucleic acid template containing the moiety. The signaling domain includes a labeled nucleic acid.

According to a first embodiment of the second aspect, the linker includes at least one member selected from the group consisting of iSp1, iSp3, iSp9 and iSp18 or combinations thereof. According to a second embodiment of the second aspect, the linker includes iSp9 or iSp18. According to a third embodiment of the second aspect, the linker includes iSp9.

According to a third embodiment of the second aspect, the labeled nucleic acid can include one of several features. According to a first feature of the third embodiment of the second aspect, the labeled nucleic acid includes a nucleic acid having a plurality of labels. According to a second feature of the third embodiment of the second aspect, the labeled nucleic acid includes a double-stranded molecule having a plurality of labels.

According to the second feature of the third embodiment of the second aspect, the plurality of labels includes a label spaced every 3-12 nucleotides. According to the second feature of the third embodiment of the second aspect, the plurality of labels includes a label spaced every 6 nucleotides. According to the second feature of the third embodiment of the second aspect, the plurality of labels includes two or more labels having discrete optical or spectroscopic properties. According to the second feature of the third embodiment of the second aspect, the plurality of labels includes a radioactive moiety, a fluorescent moiety, a chemiluminescent moiety, an enzyme, substrate for an enzyme, an antigen for an antibody, or a ligand for at least one ligand-binding molecule. According to the second feature of the third embodiment of the second aspect the plurality labels includes a fluorescent moiety or a chemiluminescent moiety. According to the second feature of the third embodiment of the second aspect, the plurality of labels includes s a fluorescent moiety. According to the second feature of the third embodiment of the second aspect, the hybridization domain includes a nucleic acid sequence lacking repetitive sequence elements.

In a third aspect, a nucleic acid hybridization probe system for detecting a nucleic acid target is provided. The nucleic acid hybridization probe system includes the following: a first oligonucleotide, a second oligonucleotide, a third oligonucleotide, a fourth oligonucleotide, and a ligase. The first oligonucleotide includes a single-stranded molecule having a first hybridization subdomain and a first signal acceptor subdomain. The second oligonucleotide includes a single-stranded molecule having a second hybridization subdomain and a second signal acceptor subdomain. The third oligonucleotide includes a single-stranded molecule having a first signal subdomain. The fourth oligonucleotide includes a single-stranded molecule having a second signal subdomain. The first hybridization subdomain and the second hybridization domain together includes a contiguous hybridization domain for binding to a contiguous complementary sequence of the nucleic acid sequence target. The first signal acceptor subdomain and the second signal acceptor subdomain when annealed together includes a signal acceptor domain having double-stranded form with a signal domain-binding site including a single-stranded form at the terminus of the signal acceptor domain. The first signal subdomain and the second signal subdomain when annealed together includes a signal domain having double-stranded form with a signal acceptor domain-binding site including a single-stranded form at the terminus of the signal domain. The signal acceptor domain-binding site and the signal domain-binding site each includes a complementary sequence capable of being ligated together in the presence of the ligase.

In a first embodiment of the third aspect, the signaling domain includes at least one label. In a second embodiment of the third aspect, the signaling domain includes a plurality of labels. In a third embodiment of the third aspect, a plurality of labels is internally incorporated into at least one member selected from the group consisting of the third oligonucleotide, the fourth oligonucleotide and combinations thereof.

In a first feature of the third embodiment of the third aspect, the plurality of labels includes a label spaced every 3-12 nucleotides. In a second feature of the third embodiment of the third aspect, the plurality of labels includes a label spaced every 6 nucleotides. In a third feature of the third embodiment of the third aspect, the plurality of labels includes two or more labels having discrete optical or spectroscopic properties. In a fourth feature of the third embodiment of the third aspect, the plurality of labels includes a radioactive moiety, a fluorescent moiety, a chemiluminescent moiety, an enzyme, substrate for an enzyme, an antigen for an antibody, or a ligand for at least one ligand-binding molecule. In a fifth feature of the third embodiment of the third aspect, the plurality of labels includes a fluorescent moiety or a chemiluminescent moiety. In a sixth feature of the third embodiment of the third aspect, the plurality of labels includes a fluorescent moiety.

In a fourth embodiment of the third aspect, the contiguous hybridization domain includes a nucleic acid sequence lacking repetitive sequence elements.

In a fifth embodiment of the third aspect, a signal amplification adaptor is additionally included. The signal amplification adaptor includes a plurality of signal amplification subdomains. Each signal amplification subdomain includes a double-stranded form having a single-stranded terminus. The single-stranded terminus includes a binding site having complementary to at least one member selected from the group consisting of a signal acceptor domain-binding site, a signal domain-binding site, and combinations thereof. In one feature of the fifth embodiment of the third aspect, the plurality of signal amplification subdomains include oligonucleotides.

In a sixth embodiment of the third aspect, a signal amplification adaptor is additionally included. The signal amplification adaptor includes the following: a first oligonucleotide, a second oligonucleotide and a third oligonucleotide. The first oligonucleotide includes a first hybridizing subdomain and a second hybridizing subdomain. The second oligonucleotide includes a third hybridizing subdomain and a fourth hybridizing subdomain. The third oligonucleotide includes a fifth hybridizing subdomain and a sixth hybridizing subdomain.

The second hybridizing subdomain is complementary to the third hybridizing subdomain. The fourth hybridizing subdomain is complementary to the fifth hybridizing subdomain. The sixth hybridizing subdomain is complementary to the first hybridizing subdomain. The first oligonucleotide and the second oligonucleotide when annealed together includes a first signal amplification subdomain having double-stranded form with a first binding site including a single-stranded form present at the terminus of the first signal amplification subdomain. The second oligonucleotide and the third oligonucleotide when annealed together includes a second signal amplification subdomain having double-stranded form with a second binding site including a single-stranded form present at the terminus of the second signal amplification subdomain. The third oligonucleotide and the first oligonucleotide when annealed together includes a third signal amplification subdomain having double-stranded form with a third binding site including a single-stranded form present at the terminus of the third signal amplification subdomain. The first, second and third binding sites are complementary to at least one member selected from the group consisting of a signal acceptor domain-binding site, a signal domain-binding site, and combinations thereof.

In a fourth aspect, a method of preparing a nucleic acid hybridization probe for detecting a nucleic acid sequence target is provided. The method includes the several steps. The first step includes fragmenting a nucleic acid including the nucleic acid sequence target to generate a population of double-stranded fragments. The second step includes flushing the termini of the population of double-stranded fragments to generate a population of flush-ended fragments. The third step includes ligating sequences including an adaptor onto each member of the population of flushed-ended fragments to generate a population of fragments containing terminal adaptor sequences; The fourth step includes optionally size-fractionating the population via gel electrophoresis to obtain a template library restricted to the size range desired; The fifth step includes subjecting the population of fragments containing terminal adaptor sequences to DNA amplification with a primer to generate a population of double-stranded molecules having a 5' single-stranded terminus. The sixth step includes denaturing the population of double-stranded molecules having a 5' single-stranded terminus to generate a population including the nucleic acid hybridization probe.

The primer includes a single-stranded molecule having the following structure: 5'-S-L-A-3'. The S includes a signaling domain, said signaling domain includes a nucleic acid having at least one label or a nucleic acid having at least one nucleic acid domain for binding at least one additional nucleic acid. The L includes a linker, said linker includes a moiety having at least one abasic site, such that the moiety blocks extension by an elongating polymerase on a nucleic acid template containing the moiety. The A includes a nucleic acid sequence corresponding to the adaptor sequence at the terminus of each member of the population of fragments containing terminal adaptor sequences and having the appropriate strand polarity to permit primer extension on the population of fragments containing terminal adaptor sequences using DNA amplification.

According to a first embodiment of the fourth aspect, the linker includes at least one member selected from the group consisting of iSp1, iSp3, iSp9 and iSp18 or combinations thereof. According to a second embodiment of the fourth aspect, the linker includes iSp9 or iSp18. According to a third embodiment of the fourth aspect, the linker includes iSp9. According to a fourth embodiment of the fourth aspect, the nucleic acid sequence target includes a genomic DNA, a cDNA or an RNA. According to a fifth embodiment of the fourth aspect, the nucleic acid sequence target includes a nucleic acid sequence lacking repetitive sequence elements.

According to a first feature of the third embodiment of the fourth aspect, the signaling domain further includes a plurality of labels. In a first implementation of this feature, the plurality of labels includes a label spaced every 3-12 nucleotides.

In a second implementation of this feature, the plurality of labels includes a label spaced every 6 nucleotides. In the second implementation of this feature, the label includes a radioactive moiety, a fluorescent moiety, a chemiluminescent moiety, an enzyme, substrate for an enzyme, an antigen for an antibody, or a ligand for at least one ligand-binding molecule. In the second implementation of this feature, the label includes a fluorescent moiety or a chemiluminescent moiety. In the second implementation of this feature, the label includes a fluorescent moiety.

In a third implementation of this feature, plurality of labels includes two or more labels having discrete optical or spectroscopic properties. In the third implementation of this feature, the signaling domain further includes a plurality of nucleic acid binding domains, wherein each nucleic acid binding domain is available for binding at least one additional nucleic acid.

In a fifth aspect, a method of detecting a nucleic acid sequence target in a sample is provided. The method includes several steps. The first step includes obtaining the sample containing the nucleic acid sequence target. The second step includes contacting the sample with a nucleic acid hybridization probe. The third step includes visualizing the hybridization signal. The nucleic acid hybridization probe is selected from the group consisting of the nucleic acid hybridization probe of the first aspect, the nucleic acid hybridization probe of second aspect and combinations thereof.

In first embodiment of the fifth aspect, the method includes two additional steps. The first additional step includes performing DNA amplification on the nucleic acid target sequence using the polymerase chain reaction (PCR). The second additional step includes visualizing the hybridization signal by quantitative PCR, real-time PCR PNA clamp-mediated PCR or digital PCR. According to one feature of the first embodiment of the fifth aspect, the nucleic acid sequence target includes a nucleic acid sequence lacking repetitive sequence elements.

In second embodiment of the fifth aspect, the method includes the one additional step. The first additional step includes immobilizing the sample onto a substrate. The substrate includes one of a particle, a membrane, a microarray substrate or a FISH assay substrate.

In a sixth aspect, a method of detecting a nucleic acid sequence target in a sample is provided. The method includes several steps. The first step includes obtaining the sample containing the nucleic acid sequence target. The second step includes contacting the sample with a nucleic acid hybridization probe system. The third step includes subjecting the sample to a ligase reaction. The fourth step includes visualizing the hybridization signal. The nucleic acid hybridization probe system includes the system of third aspect.

According to a first embodiment of the sixth aspect, the contiguous hybridization domain includes a nucleic acid sequence lacking repetitive sequence elements. According to a second embodiment of the sixth aspect, the nucleic acid hybridization probe system further includes a signal amplification adaptor. The signal amplification adaptor includes a plurality of signal amplification subdomains. Each signal amplification subdomain includes a double-stranded form having a single-stranded terminus. The single-stranded terminus includes a binding site having complementarity to at least one member selected from the group consisting of a signal acceptor domain binding site, a signal domain binding site and combinations thereof.

In a seventh aspect, a method of screening a sample for the presence of cancer cells is provided. The method includes several steps. The first step includes obtaining a sample containing a plurality of cells. The second step includes hybridizing a set of chromosomal probes to the sample. The set includes probes specific for a type of cancer associated with amplification, translocation, deletion, or rearrangement of specific nucleic acid sequence target in one or more chromosomes. The third step includes visualizing the hybridization pattern of the set of chromosomal probes in the plurality of cells in the sample. The hybridization pattern reveals the presence of at least one amplification, translocation, deletion, or rearrangement of a specific nucleic acid sequence target in the sample that is indicative of the presence of cancer cells in the sample. The set of chromosomal probes includes at least one member selected from the group consisting of a nucleic acid hybridization probe of the first aspect, a nucleic acid hybridization probe of second aspect, a nucleic acid hybridization probe system of the third aspect and combinations thereof.

In a first embodiment of the seventh aspect, the type of cancer is selected from the group consisting of prostate cancer, adrenocortical cancer, biliary cancer, breast cancer, ovarian cancer, endometrial (uterine) cancer, cervical cancer, colorectal cancer, esophageal cancer, gall bladder cancer, gastric cancer, glioma, glioblastoma, head and neck cancer, lung cancer, bladder cancer, pancreatic cancer, gastric cancer and salivary gland cancer. In a second embodiment of the seventh aspect, the sample is selected from the group consisting of urine, blood, cerebrospinal fluid, pleural fluid, sputum, peritoneal fluid, bladder washing, secretion, oral washing, tissue sample, touch prep and fine-needle aspirate. In a third embodiment of the seventh aspect, a set of chromosomal probes includes at least one nucleic acid sequence lacking repetitive sequence elements. In a fourth embodiment of the seventh aspect, the set of chromosomal probes are fluorescently labeled.

In a fifth embodiment of the seventh aspect, visualizing the hybridization pattern of the set of chromosomal probes in the plurality of cells of the sample is performed by fluorescence microscopy. According to one feature of this embodiment, fluorescence microscopy is performed with digital imaging.

In a sixth embodiment of the seventh aspect, the sample includes a tissue sample. In a seventh embodiment of the seventh aspect, the set of chromosomal probes includes one or more isolated nucleic acid sequences specific for a genetic locus. According to one feature of the seventh embodiment of the seventh aspect, the genetic locus includes at least one member selected from the group consisting of EGFRv3, CDKN2A/p16 (9p21) and p53 (17p13.1).

In an eighth aspect, a method of predicting and monitoring the status of a cancer in a patient is provided. The method includes several steps. The first step includes obtaining a sample containing a plurality of cells from the patient. The second step includes hybridizing a set of chromosomal probes to the sample, wherein the set includes probes specific for a type of cancer associated with amplification, translocation, deletion, or rearrangement of specific nucleic acid sequence target in one or more chromosomes. The third step includes visualizing the hybridization pattern of the set of chromosomal probes in the plurality of cells in the sample. The hybridization pattern reveals the presence of at least one amplification, translocation, deletion, or rearrangement of a specific nucleic acid sequence target in the sample that is indicative of the presence of cancer cells in the sample. An increase in a percentage of cancer cells in the sample is indicative of progression or recurrence of the cancer in the patient. A decrease of cancer cells in the sample is indicative of decrease or remission of the cancer in the patient. The set of chromosomal probes includes at least one member selected from the group consisting of a nucleic acid hybridization probe of the first aspect, a nucleic acid hybridization probe of the second aspect, a nucleic acid hybridization probe system of the third aspect and combinations thereof.

In a first embodiment of the eighth aspect, the type of cancer is selected from the group consisting of prostate cancer, adrenocortical cancer, biliary cancer, breast cancer, ovarian cancer, endometrial (uterine) cancer, cervical cancer, colorectal cancer, esophageal cancer, gall bladder cancer, gastric cancer, glioma, glioblastoma, head and neck cancer, lung cancer, bladder cancer, pancreatic cancer, gastric cancer, and salivary gland cancer. In a second embodiment of the eighth aspect, the sample is selected from the group consisting of urine, blood, cerebrospinal fluid, pleural fluid, sputum, peritoneal fluid, bladder washing, secretion, oral washing, tissue sample, touch prep and fine-needle aspirate. In a third embodiment of the eighth aspect, a set of chromosomal probes includes at least one nucleic acid sequence lacking repetitive sequence elements. In a fourth embodiment of the eighth aspect, the set of chromosomal probes are fluorescently labeled.

In a fifth embodiment of the eighth aspect, the step of visualizing the hybridization pattern of the set of chromosomal probes in the plurality of cells of the sample is performed by fluorescence microscopy. According to a first feature of the fifth embodiment of the eighth aspect, fluorescence microscopy is performed with digital imaging.

In a sixth embodiment of the eighth aspect, the sample includes a tissue sample. In a seventh embodiment of the eighth aspect, the set of chromosomal probes includes one or more isolated nucleic acid sequences specific for a genetic locus. According to one feature of the seventh embodiment of the eighth aspect, the genetic locus includes at least one member selected from the group consisting of EGFRv3, CDKN2A/p16 (9p21) and p53 (17p13.1).

In a ninth aspect, a method of monitoring the effectiveness of an anti-cancer therapeutic agent for treating a cancer in a patient is provided. The method includes several steps. The first step includes obtaining samples containing a plurality of cells from the patient before and after treating the patient with the anti-cancer therapeutic agent. The second step includes hybridizing a set of chromosomal probes to the samples, wherein the set includes probes specific for a type of cancer associated with amplification, translocation, deletion, or rearrangement of specific nucleic acid sequence target in one or more chromosomes. The third step includes visualizing the hybridization pattern of the set of chromosomal probes in the plurality of cells in the samples. The hybridization pattern reveals the presence of at least one amplification, translocation, deletion, or rearrangement of a specific nucleic acid sequence target in the samples that is indicative of the presence of cancer cells in the samples. An increase in a percentage of cancer cells in the sample following treating the patient with the anti-cancer therapeutic agent as compared to the percentage of cancer cells in the sample before treating the patient with the anti-cancer therapeutic agent is indicative of the anti-cancer therapeutic agent being ineffective. A decrease in a percentage of cancer cells in the sample following treating the patient with the anti-cancer therapeutic agent as compared to the percentage of cancer cells in the sample before treating the patient with the anti-cancer therapeutic agent is indicative of the anti-cancer therapeutic agent being effective. The set of chromosomal probes includes at least one member selected from the group consisting of a nucleic acid hybridization probe of the first aspect, a nucleic acid hybridization probe of the second aspect, a nucleic acid hybridization probe system of the third aspect and combinations thereof.

In a first embodiment of the ninth aspect, the type of cancer is selected from the group consisting of prostate cancer, adrenocortical cancer, biliary cancer, breast cancer, ovarian cancer, endometrial (uterine) cancer, cervical cancer, colorectal cancer, esophageal cancer, gall bladder cancer, gastric cancer, glioma, glioblastoma, head and neck cancer, lung cancer, bladder cancer, pancreatic cancer, gastric cancer, and salivary gland cancer. In a second embodiment of the ninth aspect, the sample is selected from the group consisting of urine, blood, cerebrospinal fluid, pleural fluid, sputum, peritoneal fluid, bladder washing, secretion, oral washing, tissue sample, touch prep and fine-needle aspirate. In a third embodiment of the ninth aspect, a set of chromosomal probes includes at least one nucleic acid sequence lacking repetitive sequence elements. In a fourth embodiment of the ninth aspect, the set of chromosomal probes are fluorescently labeled.

In a first embodiment of the ninth aspect, the step of visualizing the hybridization pattern of the set of chromosomal probes in the plurality of cells of the sample is performed by fluorescence microscopy. In a first feature of the first embodiment of the ninth aspect, fluorescence microscopy is performed with digital imaging.

In a fifth embodiment of the ninth aspect, the sample includes a tissue sample. In a sixth embodiment of the ninth aspect, the set of chromosomal probes includes one or more isolated nucleic acid sequences specific for a genetic locus. In a first feature of the sixth embodiment of the ninth aspect, the genetic locus includes at least one member selected from the group consisting of EGFRv3, CDKN2A/p16 (9p21) and p53 (17p13.1).

In a tenth aspect, a method of diagnosing a patient for the presence of a cancer is provided. The method includes several steps. The first step includes obtaining a sample from the patient containing a plurality of cells. The second step includes hybridizing a set of chromosomal probes to the sample The set includes probes specific for a type of cancer associated with amplification, translocation, deletion, or rearrangement of specific nucleic acid sequence target in one or more chromosomes. The third step includes visualizing the hybridization pattern of the set of chromosomal probes in the plurality of cells in the sample. The hybridization pattern reveals the presence of at least one amplification, translocation, deletion, or rearrangement of a specific nucleic acid sequence target in the sample that is indicative of the presence of cancer cells in the sample. The set of chromosomal probes includes at least one member selected from the group consisting of a nucleic acid hybridization probe of the first aspect, a nucleic acid hybridization probe of the second aspect, a nucleic acid hybridization probe system of the third aspect and combinations thereof.

In a first embodiment of the tenth aspect, the type of cancer is selected from the group consisting of prostate cancer, adrenocortical cancer, biliary cancer, breast cancer, ovarian cancer, endometrial (uterine) cancer, cervical cancer, colorectal cancer, esophageal cancer, gall bladder cancer, gastric cancer, glioma, glioblastoma, head and neck cancer, lung cancer, bladder cancer, pancreatic cancer, gastric cancer, and salivary gland cancer. In a second embodiment of the tenth aspect, the sample is selected from the group consisting of urine, blood, cerebrospinal fluid, pleural fluid, sputum, peritoneal fluid, bladder washing, secretion, oral washing, tissue sample, touch prep and fine-needle aspirate. In a third embodiment of the tenth aspect, a set of chromosomal probes includes at least one nucleic acid sequence lacking repetitive sequence elements. In a fourth embodiment of the tenth aspect, the set of chromosomal probes are fluorescently labeled.

In a fifth embodiment of the tenth aspect, visualizing the hybridization pattern of the set of chromosomal probes in the plurality of cells of the sample is performed by fluorescence microscopy. According to one feature of the fifth embodiment of the tenth aspect, fluorescence microscopy is performed with digital imaging.

In a sixth embodiment of the tenth aspect, the sample includes a tissue sample. In a seventh embodiment of the tenth aspect, the set of chromosomal probes includes one or more isolated nucleic acid sequences specific for a genetic locus. According to one feature of the seventh embodiment of the tenth aspect, the genetic locus includes at least one member selected from the group consisting of EGFRv3, CDKN2A/p16 (9p21) and p53 (17p13.1).

In an eleventh aspect, a method of proving a prognosis for patient suspects of having a cancer is provided. The method includes several steps. The first step includes obtaining a sample containing a plurality of cells. The second step includes hybridizing a set of chromosomal probes to the sample, wherein the set includes probes specific for a type of cancer associated with amplification, translocation, deletion, or rearrangement of specific nucleic acid sequence target in one or more chromosomes. The third step includes visualizing the hybridization pattern of the set of chromosomal probes in the plurality of cells in the sample. The hybridization pattern reveals the presence of at least one amplification, translocation, deletion, or rearrangement of a specific nucleic acid sequence target in the sample that is indicative of the presence of cancer cells in the sample. The set of chromosomal probes includes at least one member selected from the group consisting of a nucleic acid hybridization probe of the first aspect, a nucleic acid hybridization probe of the second aspect, a nucleic acid hybridization probe system of the third aspect and combinations thereof.

In a first embodiment of the eleventh aspect, the type of cancer is selected from the group consisting of prostate cancer, adrenocortical cancer, biliary cancer, breast cancer, ovarian cancer, endometrial (uterine) cancer, cervical cancer, colorectal cancer, esophageal cancer, gall bladder cancer, gastric cancer, glioma, glioblastoma, head and neck cancer, lung cancer, bladder cancer, pancreatic cancer, gastric cancer, and salivary gland cancer. In a second embodiment of the eleventh aspect, the sample is selected from the group consisting of urine, blood, cerebrospinal fluid, pleural fluid, sputum, peritoneal fluid, bladder washing, secretion, oral washing, tissue sample, touch prep and fine-needle aspirate. In a third embodiment of the eleventh aspect, a set of chromosomal probes includes at least one nucleic acid sequence lacking repetitive sequence elements. In a fourth embodiment of the eleventh aspect, the set of chromosomal probes are fluorescently labeled.

In a fifth embodiment of the eleventh aspect, visualizing the hybridization pattern of the set of chromosomal probes in the plurality of cells of the sample is performed by fluorescence microscopy. In a first feature of the fifth embodiment of the eleventh aspect, fluorescence microscopy is performed with digital imaging.

In a sixth embodiment of the eleventh aspect, the sample includes a tissue sample. In a seventh embodiment of the eleventh aspect, the set of chromosomal probes includes one or more isolated nucleic acid sequences specific for a genetic locus. In a first feature of the seventh embodiment of the eleventh aspect, the genetic locus includes at least one member selected from the group consisting of EGFRv3, CDKN2A/p16 (9p21) and p53 (17p13.1).

In a twelfth aspect, a kit consisting of a set of chromosomal probes and optionally one or more reagents selected from the group consisting of a slide, phosphate buffered saline, hybridization buffer, 4,6-diamidino-2-phenylindole dihydrochloride, sodium chloride-sodium citrate solution, fixative, ethanol, non-ionic detergent, and denaturation buffer is provided. The set of chromosomal probes includes at least one member selected from the group consisting of a nucleic acid hybridization probe of the first aspect, a nucleic acid hybridization probe of the second aspect, a nucleic acid hybridization probe system of the third aspect and combinations thereof. The probes are labeled such that each probe can be distinctly visualized after hybridization to a biological sample.

In a first embodiment of the twelfth aspect, the set of chromosomal probes includes one or more isolated nucleic acid sequences specific for a genetic locus. According to a first feature of this embodiment, the genetic locus includes at least one member selected from the group consisting of EGFRv3, CDKN2A/p16 (9p21) and p53 (17p13.1).

In a second embodiment of the twelfth aspect, a set of chromosomal probes includes at least one nucleic acid sequence lacking repetitive sequence elements.

The invention will be further described in the following examples, which do not limit the scope of the invention described in the claims.

EXAMPLES

Example 1. Nucleic Acid Oligonucleotide Reagents

The oligonucleotides used for this example are presented in Table 1.

TABLE 1

| SEQ ID NO: | Sequence (5'→3') |
|---|---|
| 1 | CATGAACAATAACTAAGACAAGTTCTGTATCTATGTCTTATTCTAAAACTGA TACTGAGACTTTGTCAGAATC/iSp9/GGAGATGAGTGGATGGGAGAGAAGTG |
| 2 | CATGAACAATAACTAAGACAAGTTCTGTATCTATGTCTTATTCTAAAACTGAT ACTGAGACTTTGTCAGAATC/iSp9/GTGGTAGGAGGGATGAATGTGAGTG |
| 3 | GCTCTGATTATGCCACCGTCCTTGATT.GCTCTGATTATGCCACCGTCCTTGATT. GCTCTGATTATGCCACCGTCCTTGATT/iSp9/GCGATTCCGACACTCACC |
| 4 | GCCTCGCTCCAGACCTTGATACCGTTT.GCCTCGCTCCAGACCTTGATACCGTTT. GCCTCGCTCCAGACCTTGATACCGTTT/iSp9/GCGATTCCGACACTCACC |

TABLE 1 -continued

| SEQ ID NO: | Sequence (5'→3') |
|---|---|
| 5 | AAGAGCTGAGACGGAGTCAGGAGC.AAGAGCTGAGACGGAGTCAGGAGC.<br>AAGAGCTGAGACGGAGTCAGGAGC.AAGAGCTGAGACGGAGTCAGGAGC.<br>AAGAGCTGAGACGGAGTCAGGAGC.AAGAGCTGAGACGGAGTCAGGAGC.<br>AAGAGCTGAGACGGAGTCAGGAGC.AATCAAGGACGGTGGCATAATCAGAGC |
| 6 | TGGTGCTAGTTCTGGAGCTTGTGC.TGGTGCTAGTTCTGGAGCTTGTGC.<br>TGGTGCTAGTTCTGGAGCTTGTGC.TGGTGCTAGTTCTGGAGCTTGTGC.<br>TGGTGCTAGTTCTGGAGCTTGTGC.TGGTGCTAGTTCTGGAGCTTGTGC.<br>TGGTGCTAGTTCTGGAGCTTGTGC.AAACGGTATCAAGGTCTGGAGCGAGGC |
| 7 | AATCAAGGACGGTGGCATAATCAGAGC/iSp9/GCGATTCCGACACTCACC |
| 8 | AAACGGTATCAAGGTCTGGAGCGAGGC/iSp9/GCGATTCCGACACTCACC |
| 9 | AATCAAGGACGGTGGCATAATCAGAGC/iSp9/GGAGATGAGTGGATGGGAGAGAAGTG |
| 10 | AATCAAGGACGGTGGCATAATCAGAGC/iSp9/GTGGTAGGAGGGATGAATGTGAGTG |
| 11 | /5Phos/GGTGAGTGTCGGAATCGCAG |
| 12 | ATCTGCGATTCCGACACTCACC |
| 13 | /5TET/ATCTGCGATTCCGACACTCACC |
| 14 | /5Phos/GCAGTTCGGCAGAATCAGGC |
| 15 | TTGCCTGATTCTGCCGAACTGC |
| 16 | /5TET/TTGCCTGATTCTGCCGAACTGC |
| 17 | GGAGATGAGTGGATGGGAGAGAAGTGAGGTTGAGTG |
| 18 | CACTCAACCT |
| 19 | GTGGTAGGAGGGATGAATGTGAGTGTGAGAATGGAG |
| 20 | CTCCATTCTC |

SEQ ID NOs:1 and 2 contain the same 5' signaling region, with cytosine every 6 bases. An iSp9 spacer separates the signaling region from the primer region. For both SEQ ID NOs:1 and 2, the primer region contains no cytosine groups, so modification of the oligonucleotides via bisulfite/ethylenediamine leaves this portion unaffected. The primer regions differ for SEQ ID NOs:1 and 2 to avoid inhibitory stem-loop structures from forming during DNA amplification.

SEQ ID NOs:3 and 4 have identical 3' primer regions, but different 5' signaling regions. In both SEQ ID NOs:3 and 4, the 5' signaling portion is composed of three identical sequences (separated by period symbols in Table 1). These sequences represent examples of 106 for one preferred embodiment of structure 100.

SEQ ID NOs:5 and 6 represent examples of 107 designed to carry signaling agent and bind SEQ ID NOs:3 and 4, respectively. The 3' ends of SEQ ID NOs:5 and 6 are complementary to the signaling blocks of SEQ ID NOs:3 and 4. The 5' ends of SEQ ID NOs:5 and 6 include 7 identical blocks of sequence (separated by period symbols in Table 1). For each of SEQ ID NOs:5 and 6, cytosine appears as every sixth base for the entire oligonucleotide.

The procedure used to label the oligonucleotide places fluorophores only at the cytosines. The spacing allows a high level of fluorophore incorporation while holding the fluorophores at a distance to minimize self-quenching of the fluorescence.

SEQ ID NOs:7 and 8 are designed as intermediates in preparation of a 113 that binds to the signaling blocks found in SEQ ID NOs:3 and 4, respectively. The 5' ends of SEQ ID NOs:7 and 8 have sequence complementarity to the sequences of the signaling blocks of SEQ ID NOs:3 and 4. The 3' ends of SEQ ID NOs:7 and 8 serve as primers for amplifying the DNA sequence chosen for fluorescent labeling. Both SEQ ID NOs:7 and 8 also include an iSp9 group that separates the 3' primer region from the 5' region for each oligonucleotide.

The sequences of the primer regions of SEQ ID NOs:7 and 8 3' to the iSp9 group are identical the corresponding sequences of the adaptors used in preparation of libraries for targeting agents.

Example 2. Preparation of Labeled SEQ ID NOs:1 and 2

A. Amination of SEQ ID NOs:1 and 2:

To individual 40 µL aqueous solutions of SEQ ID NOs:1 and 2 (1000 µM), 160 µL of amination reagent (500 µL water, 300 µL TFA, 174 µL ethylenediamine and 95 mg $Na_2S_2O_3$) was added. The resultant mixtures were vortexed and placed into an 80° C. water bath for 40 min, followed by desalting into water. The products were precipitated with isopropanol and sodium acetate and resuspended in 100 µL water to give SEQ ID NO:1-AM and SEQ ID NO:2-AM. The concentrations of SEQ ID NO:1-AM and SEQ ID NO:2-AM were determined spectrophotometrically at 260 nm to be 9818 μg/mL and 7409 μg/mL, respectively.

B. Conjugation of Fluorophore Labels to SEQ ID NO:1-AM and SEQ ID NO:2-AM:

A 2 μL volume of 1M NaOH was added to individual 50 μL aqueous samples containing SEQ ID NO:1-AM or SEQ ID NO:2-AM. After 1 min, a 50 μL of a mixture of DMSO/TMEDA/NaCl solution (50 μL DMSO, 50 μL of a mixture of 500 mM tetramethylethylenediamine and 2M NaCl at pH 9.1) was added to the solutions. The respective mixtures were vortexed, and 3 μL of a 100 mM TAMRA (5-(and-6)-carboxytetramethylrhodamine, succinimidyl ester (also known as Spectrum Orange [SO]) (Life Technologies™, Grand Island, N.Y.)) in DMSO solution was added to each mixture. The mixtures were vortexed and placed in a 60° C. oven for 75 min. The products were precipitated with ethanol and sodium acetate. The precipitates were washed with 85% ethanol, dried, resuspended in water, desalted into water to give 500 μL each of SEQ ID NO:1-SO and SEQ ID NO:2-SO containing a labeled SO moiety. The amount of label incorporated into each oligonucleotide was determined spectrophotometrically using extinction coefficient data at 260 nm and 560 nm. The labeled SEQ ID NO:1-SO had a yield of 341 μg with approximately 7.1 dye molecules per oligonucleotide. The labeled SEQ ID NO:2-SO had a yield of 285 μg with 7.7 dye molecules per oligonucleotide.

Example 3. Preparation of Labeled SEQ ID NOs:5 and 6 (Signaling Agents)

A. Amination of SEQ ID NOs:5 and 6:

To a 20 μL volume of 10 mg/mL SEQ ID NOs:5 or 6 in water, a 180 μL volume of an amination reagent (1.0 mL water, 600 μL TFA, 348 μL ethylenediamine and 190 mg $Na_2S_2O_3$) was added. Each solution was placed into a 65° C. water bath for 30 min, desalted into water and concentrated by ultrafiltration to a final volume of 120 μL. The concentrations of the SEQ ID NO:5-AM and SEQ ID NO:6-AM were determined spectrophotometrically. The concentrations of SEQ ID NO:5-AM and SEQ ID NO:6-AM were 840 μg/mL and 1329 μg/mL, respectively.

B. Conjugation of Fluorophore Labels to SEQ ID NO:5-AM and SEQ ID NO:6-AM:

SEQ ID NO:5-AM and SEQ ID NO:6-AM were conjugated to the activated labels 5(6)-SFX (6-(fluorescein-5-(and-6)-carboxamido) hexanoic acid, succinimidyl ester) (also known as Spectrum Green [SG]) and 5(6)-TAMRA, SE 5-(and-6)-carboxytetramethylrhodamine, succinimidyl ester (also known as Spectrum Orange [SO]) (Life Technologies™, Grand Island, N.Y.). A 30 μL volume of DMSO/TMEDA/NaCl (60 μL DMSO, 60 μL of a mixture of 500 mM tetramethylethylenediamine and 2M NaCl at pH 9.1) was added to a 30 μL volume of each SEQ ID NO:5-AM or SEQ ID NO:6-AM. Each mixture was vortexed, and a 2 μL volume of active label at 100 mM in DMSO was added. The mixtures were vortexed again and placed at 56° C. for 2 h. The labeled products were isolated by ethanol precipitation, desalted via Sephadex G25 chromatography, giving 300 μL of each labeled product. Spectroscopic measurements indicated label incorporation of 8-9%, or about 16 fluorophores per 195-base oligonucleotide.

Example 4. Preparation of Adaptor-Containing Fragment Libraries

An *E. coli* clone containing a BAC (Bacterial Artificial Chromosome) with 212 kbp of DNA corresponding to the 9p21 locus of the humane genome was cultured and the DNA isolated by methods known to the art.

The isolated DNA was sonicated to give fragments ranging from about 100 bp to 600 bp. The Fast DNA End Repair™ kit (Fermentas Inc. (Glen Burnie, Md.)) was used according to the manufacturer's instructions to flush the fragment ends.

Synthetic oligonucleotides and their complements corresponding to the desired adaptors were annealed together in the following manner. Individual 100 μM solutions of SEQ ID NOs: 17-20 were prepared in water. A volume of each resultant solution and a volume of 20× annealing buffer (1M NaCl, 200 mM Tris and 20 mM EDTA) were combined to give a single solution containing 25 μM of SEQ ID NOs: 17-20 in 1× annealing buffer. The resultant mixture was heated to 100° C. for 5 min. and allowed to cool slowly to room temperature. Thus, SEQ ID NOs:17 and 18 were annealed to form an adaptor designated adGa, and SEQ ID NOs:19 and 20 were annealed to form an adaptor designated adGb. The resultant partially double-stranded adaptors, adGa and adGb, had one flush end compatible with being ligated to the flush-ended fragment library and the other end having an non-self-complementary single-stranded end so as to prevent its participation in ligation.

A mixture of 1 μg (~8 pmole based on an average fragment length of 200 nucleotides) of flush-ended 9p21 DNA library fragments and 50 pmole of each adaptor adGa and adGb were incubated with T4 DNA ligase in a total 20 μL volume according to manufacturer's instructions (K1422; Fementas Inc. (Glen Burnie, Md.)). After ligation, the ligase was inactivated and unligated adaptors were dissociated by heating the reaction mixture at 75° C. for 5 min. The resulting overhangs on the adaptor-containing fragment library were filled in by adding 15 μL of 2×PCR Master Mix (K1071; Fermentas Inc. (Glen Burnie, Md.)) and heating the reaction mixture at 72° C. for 5 min.

The same procedure was performed simultaneously with a similarly prepared EGFRv3 fragment library from a plasmid containing approximately 15 kbp including the human EGFRv3 locus.

Example 5. Size-Selection of Adaptor-Containing Fragment Libraries

The adaptor-containing 9p21 and EGFRv3 fragment libraries were resolved on a 3% agarose gel by electrophoresis, along with appropriate DNA size markers. Ethidium bromide was used to visualize the DNA in the gel. Gel slices corresponding to fragment sizes centered at 120 bp, 150 bp, 180 bp and 200 bp were taken from the gel and heated in ~10 volumes of water to release the fragments ("gel melt volumes").

Example 6. DNA Amplification of Fragment Libraries with Primers Carrying iSp9-Linked Portions Fifty microliter aqueous mixtures were prepared that contained 25 μL of 2×PCR Master Mix (K1071; Fermentas Inc. (Glen Burnie, Md.)), 0.5 μM each of SEQ ID NOs:1 and 2, and 3 μL of each gel melt volume. These mixtures were placed on a thermocycler with the program: (a) 95° C. for 4 min, (b) 25 cycles (95° C. for 30 sec., 60° C. for 30 sec., 72° C. for 120 sec.), and (c) 72° C. for 5 min. Electrophoresis following DNA amplification showed PCR products corresponding to the expected sizes. Two-closely spaced bands were seen for each reaction: one band corresponded to the duplexed product and another band appearing at slightly higher MW corresponded to product duplexed only at the adaptor ends.

Example 7. Preparative PCR of Select 9p21 and EGFRv3 Size Fractions

Individual 100 μL aqueous reaction mixtures were prepared containing 25 μl of 2×PCR Master Mix, 2 μM final concentration of each SEQ ID NO:1-SO and SEQ ID NO:2-SO and 2 μL of templates (1 pmole) obtained from Example 6. The reaction mixtures were placed in a thermocycler set with the following thermocycling program: 15 cycles (95° C. for 30 sec., 60° C. for 30 sec., 72° C. for 3 min.). After completion of thermocycling, the reaction products were isolated by precipitation with polyethylene glycol, resuspended in TE buffer, and the concentrations measured by spectrophotometery.

Example 8. Preparation of Targeting Reagents for Indirect FISH

SEQ ID NOs:11 and 12 form a complementary pair containing a phosphorylated flush end. When SEQ ID NOs:11 and 12 are annealed, the resultant adaptor adH1 can be ligated to another flush-ended DNA sequence. The oligonucleotides having SEQ ID NOs:14 and 15 form a similar adaptor having a different sequence (adH2). The oligonucleotides having SEQ ID NOs:13 and 16 differ from SEQ ID NOs:14 and 15 only in the presence of a 5' TET fluorophore. While SEQ ID NOs:13 and 16 can be used to make adaptors, these oligonucleotides serve primarily as primers in preparatory PCR to generate PCR products having 5'-TET fluorophore labels. The purpose of the 5'-TET fluorophore label is to monitor the progress of the restriction digestion after production of the amplified product. Exposure of the resultant PCR products to the Hinfl restriction enzyme cleaves a Hinf1 site designed into the adaptor, releasing the 5'-TET fluorophore and generating a HinfI-compatible overhang on the amplified product.

Individual 1000 μM aqueous solutions of SEQ ID NOs:11, 13, 14 and 16 were prepared. Individual 30 μl volumes each of SEQ ID NOs:11 and 13 were combined with 3 μL of 20× annealing buffer (1M NaCl, 200 mM Tris and 20 mM EDTA) to form a first mixture. Individual 30 μL volumes each of SEQ ID NOs:14 and 16 were combined with 3 μL of 20× annealing buffer (1M NaCl, 200 mM Tris and 20 mM EDTA) to form a second mixture. The first and second mixtures were incubated at 100° C. for 5 min. and permitted to cool slowly at room temperature to form adH1F and adH2F, respectively.

Individual 30 μl volumes each of SEQ ID NOs:12 and 13 were combined with 3 μL of 20× annealing buffer (1M NaCl, 200 mM Tris and 20 mM EDTA) to form a first mixture. Individual 30 μl volumes each of SEQ ID NOs:14 and 15 were combined with 3 μL of 20× annealing buffer (1M NaCl, 200 mM Tris and 20 mM EDTA) to form a second mixture. The first and second mixtures were incubated at 100° C. for 5 min. and permitted to cool slowly at room temperature to form adH1 and adH2, respectively.

Preparation of EGFRv3 Probes:

EGFRv3 DNA was prepared from a plasmid source by means known to the art. This DNA was sonicated to give fragments ranging from about 100 bp to about 600 bp, then treated with Hinfl restriction enzyme (New England Biolabs Inc. (Ipswich, Mass.)) according to manufacturer's instructions. The Quick Blunting™ kit (New England Biolabs Inc. (Ipswich Mass.)) was used to flush the ends of a 20 μg sample of the sonicated DNA.

Adaptors were ligated onto the resultant flush-ended EGFRv3 fragments in the following manner. An aqueous solution was prepared that contained 2 μl of each of 100 μM adH1F and adH2F solutions, 6 μL water, 2 μL 10× ligase buffer and 10 μg flush-ended EGFRv3 fragments. A 2 μL volume of 5 U/μL ligase (Fermentas Inc. (Ann Arbor, Mich.)) was added to this aqueous solution. The resultant mixture was vortexed and incubated at room temperature for 1 h. Thereafter, a 10 μL volume of 2× Quick Ligation Reaction™ Buffer (contains PEG; New England Biolabs Inc. (Ipswich, Mass.)) was added to the reaction mixture. The reaction mixture was vortexed and incubated at room temperature for 30 min. Thereafter, a 10 μL volume of 2× Quick Ligation Reaction™ Buffer was added to the mixture. The mixture was vortexed and incubated at room temp 30 min. Thereafter, water (60 μL), 3M NaAc (20 μL) and EtOH (300 μL) were added to the mixture. The mixture was vortexed and incubated at −20° C. The DNA precipitate was collected by centrifugation, washed with 70% aqueous EtOH, air-dried and resuspended in water (50 μL). The resulting DNA sample was purified using a Purelink™ PCR purification kit (Life Technologies™ (Grand Island, N.Y.)) according to manufacturer's instructions. The final purified product was obtained at a concentration of 80 μg/mL.

The final purified product was loaded onto 1.5% agarose-EtBr gels and subjected to electrophoresis. Sections of the gel corresponding to sizes centered at 200 bp, 250 bp and 300 bp were excised and added to individual tubes containing 20 μL of TAE buffer and 2 μL of 0.5 U/μL Agarase (Fermentas Inc. (Glen Burnie, Md.)). The respective gel samples were crushed in the solutions, vortexed, and incubated in a 42° C. oven for 24 h. These samples are the EGFRv3 templates used for the DNA amplification procedures.

Preparation of 9p21 Probes:

A sample of 9p21 DNA was sonicated by means known to the art to give a distribution of fragments ranging from about 80 bp to about 500 bp. A 100 μg sample of the sonicated material was fractionated with polyethylene glycol to give a higher MW fraction (9SH) and a lower MW fraction (9SL). These fractions were individually resuspended in 20 μL of TE buffer. The concentrations were measured spectrophotometrically; the 9SH fraction and the 9SL fraction had concentrations of 2975 μg/mL and 815 μg/mL, respectively. Electrophoresis studies showed the 9SH fraction had a size class ranging from 120 bp-500 bp and the 9SL fraction had a size class ranging from 80 bp-150 bp.

Samples (10 μg) of each 9p21sonicated fraction (9SH and 9SL) were treated with Quick Blunting™ kit (New England Biolabs, Inc. (Ipswich, Mass.)) to produce flush-ended fractions having flushed ends (9SHB and 9SLB) in accordance with the manufacturer's instructions. The 9SHB and 9SLB samples were then purified using a PureLink™ PCR Purification kit (Life Technologies™ (Grand Island, N.Y.)), in accordance with the manufacturer's instructions. The resultant concentrations of 9SHB and 9SLB were 173 μg/mL and 182 μg/mL, respectively.

To 5 μg of each of the flush-ended DNA fragment samples, 9SHB and 9SLB, the following components were added: water (42 μL), 500 μM of adH1 and adH2 (2 μL of each adaptor solution), 10× ligase buffer (6 μL), and 50% aqueous PEG4000 (6 μL). The reaction mixtures were vortexed, and a 2 μL volume of 5 U/μL T4 DNA ligase (Fermentas Inc. (Glen Burnie, Md.)) was added. The ligation mixtures were incubated at room temperature for 1 h. The DNA was isolated using a PureLink™ PCR Purification kit (Life Technologies™ (Grand Island, N.Y.)) in accordance with the manufacturer's instructions to give adaptor-containing product size classes (9SHA and 9SLA) in 50 µL volumes. The concentrations of the 9SHA and 9SLA samples were 168 µg/mL and 172 µg/mL, respectively.

Preparative PCR of EGFRv3 with SEQ ID NO:3 and 9p21 with SEQ ID NO:4:

To 400 µL water in each of 2 tubes was added 1 µL of one of the following templates: adaptor-containing EGFRv3 DNA fragments (EM) or adaptor-containing 9p21 DNA fragments (9SLA). An 8 µL volume of SEQ ID NO:3 (1000 µM) was added to the EM tube. An 8 µL volume of SEQ ID NO:4 (1000 µM) was added to the 9SLA tube. A 400 µL volume of 2×PCR Master Mix (Fermentas Inc. (Glen Burnie, Md.)) was added to both tubes. The samples were subjected to amplification with a thermocycling program set for 25 cycles (95° C. 30 sec.; 53° C. 30 sec.; 73° C. 60 sec.). Ultrafiltration units having a cutoff of 10 kDa (Nanosep®; Pall Corp. (Ann Arbor, Mich.)) were used to concentrate the samples after PCR amplification. The PCR products were washed, resuspended in water (200 µL) and extracted with an equal volume of phenol/chloroform/isoamyl alcohol. The aqueous phases were subjected to ethanol precipitation and the collected DNA precipitates were resuspended in water (200 µL). The resultant labeled probes, EGFRv3-b1 and 9p21-b2, were obtained at concentrations of 929 µg/mL and 724 µg/mL, respectively.

Example 9. FISH Hybridization Conditions

The targeting probes were hybridized to human chromosomal DNA in lymphocytes bound to glass microscope slides by methods known in the art. In a typical experiment the reagent mixture consists of 7 µL of LSI/WCP hybridization buffer (Abbott Molecular (Des Plaines, Ill.)) and 3 µL water containing 2000 ng sonicated human placental DNA, 500 ng $C_ot$-1 DNA (Life Technologies™ (Grand Island, N.Y.)), and 100 ng each of EGFRv3-b1 and 9p21-b2.

The microscope slide was dehydrated by successive immersion in 70%, 85% and 100% ethanol, then air dried. The test solution (10 µL) was placed on the slide and covered with a 22×22 mm slip, causing the solution to spread over the covered area. Rubber cement was applied to seal the edges and the slide placed in an instrument that controls the temperature. The temperature was raised to 73° C. for 3 min. to denature the DNA of both the sample and the reagent, then lowered to 37° C. for an extended period, typically 16-20 h to allow time for the reagent to hybridize to its target. After completion of the hybridization time, the rubber cement and slips were removed, and the slide washed 2 min. in a solution of 0.4×SSC and 0.3% NP40 at 73° C., then in 2×SSC, 0.1% NP40 at room temperature, then air dried.

For use of directly-labeled probes, the reporting agent was bound using the described procedure. For use of indirectly-labeled probes, another hybridization and wash step was performed to bind the reporting agent to the common binding groups on the targeting agent. The hybridization probes and the reporting agent are comprised of single stranded DNA; therefore, no denaturing step was needed. Additionally, hybridization can be completed in much shorter time since the reporter sequence and its complement (the signaling block) are at much higher effective concentration than any specific sequence stretch of the targeting agent.

For directly-labeled probes, the slide was prepared for viewing by placing 10 µL of a solution of DAPI on the target area and covering with a slip. The slide was viewed with a fluorescence microscope equipped with filters suitable for the fluorophore of interest. The following procedure was used for FISH hybridization assays using indirectly-labeled probes (indirect FISH).

A. First Hybridization:

Hybridization Reagent A was prepared that contained the following components: 16 µg of sonicated human placental DNA, 4.0 µg of $C_ot$-1 DNA (Life Technologies™, (Grand Island, N.Y.)), 0.8 µg of CEP7-SG (Abbott Molecular (Des Plaines, Ill.)), 0.8 µg each of EGFRv3-b1 and 9p21-b2 in 24 µL water, and 56 µL LSI/WCP hybridization buffer (Abbott Molecular (Des Plaines, Ill.)).

Four Human Male Lymphocyte slides (Abbott Molecular (Des Plaines, Ill.)) were dehydrated by successive immersion in 70%, 85% and 100% ethanol, then air dried. A 20 µL volume of Hybridization Reagent A was streaked down the center of each slide, then covered with 22×50 mm slips and the edges sealed with rubber cement. The slides were placed on a Hybrite hybridization instrument and the temperature programmed to 73° C. for 3 min. followed by 37° C. for 16 h. After completion of the program, the slips were removed and the slides washed in 0.4×SSC 0.3% NP40 for 2 min. at 73° C., followed by another wash in 2×SSC-0.1% NP40 for 1 min. at room temperature. The sample was then air dried.

B. Second Hybridization

The following signaling reagent for indirect FISH was prepared: 10 nM SEQ ID NO:5-SO and 10 nM SEQ ID NO:6-SG in 10% dextran sulfate, 1×SSC, 0.2% NP40.

A 10 µL volume of the signaling reagent was added the sample, and the sample was covered with coverslips. After incubation on Hybrite at 55° C. for 10 min, the coverslips were removed, and the slide was washed in 0.4×SSC-0.3% NP40 at 55° C. for 2 min, followed by another wash in 2×SSC-0.1% NP40 at room temperature for 1 min, and air dried. Owing to the short time associated with the second hybridization it was unnecessary to seal the edges with rubber cement.

Example 10. Fluorescence Microscopy of Resultant Hybridization Patterns

The slide was treated with DAPI-II, covered with a 22×50 mm slip and viewed under fluorescence microscope equipped with filters that allow simultaneous visualization of DAPI, fluorescein (green) and TAMRA (orange) signals. The photograph illustrated the expected green signals on metaphase chromosomes consistent with that expected for CEP7. Immediately adjacent to one of these was a small orange signal consistent with hybridization at the locus for EGFR. Additionally, green signals consistent with hybridization at the 9p21 locus (and its usual appearance as a pair of signals on adjacently aligned chromosomes) were present in the metaphase spread. A closeby nucleus showed two signals for CEP7-SG associated with closely located orange signals for EGFR. Only one additional green signal consistent with hybridization to the 9p21 locus was noted on the partial image.

Other Embodiments

It is understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims. While various embodiments of the invention have been described, it will be apparent to those of ordinary skill in the art that other embodiments and implementations are possible within the scope of the invention. Accordingly, the invention is not to be restricted except in light of the attached claims and their equivalents.

What is claimed is:

1. A nucleic acid hybridization probe for detecting a nucleic acid target sequence, said nucleic acid hybridization probe consists of structure (I):

$$5'\text{-S-L-A-H-}3' \quad (I),$$

wherein
H is a hybridization domain,
A is an adaptor,
L is a linker, and
S is a signaling domain,
wherein
the hybridization domain comprises a nucleic acid sequence having complementarity to the nucleic acid target sequence,
the adaptor comprises a nucleic acid sequence,
the linker comprises a moiety having at least one abasic site consisting of iSp3, iSp9 or iSp18,
the signaling domain consists of a nucleic acid having at least one chemically modified nucleobase covalently attached to a label,
wherein the label consists of a member selected from a group consisting of a fluorescent moiety, a chemiluminescent moiety, an enzyme, substrate for an enzyme, an antigen for an antibody, and a ligand for at least one ligand-binding molecule,
wherein the hybridization domain comprises a 3'-OH terminus.

2. The nucleic acid hybridization probe of claim 1, wherein the signaling domain comprises a plurality of chemically modified nucleobases covalently attached to labels.

3. The nucleic acid hybridization probe of claim 2, wherein the plurality of chemically modified nucleobases covalently attached to labels comprises a chemically modified nucleobase covalently attached to a label spaced every 3-12 nucleotides.

4. The nucleic acid hybridization probe of claim 2, wherein the labels comprise two or more labels having discrete optical or spectroscopic properties.

5. The nucleic acid hybridization probe of claim 1, wherein the hybridization domain comprises a nucleic acid sequence lacking repetitive sequence elements.

6. The nucleic acid hybridization probe of claim 1, wherein any nucleic acid sequence present in structure (I) having complementary to the target nucleic acid target sequence resides in the hybridization domain.

7. A method of preparing the nucleic acid hybridization probe of claim 1, said method comprises:
fragmenting a nucleic acid comprising the nucleic acid target sequence target to generate a population of double-stranded fragments;
flushing the termini of the population of double-stranded fragments to generate a population of flush-ended fragments;
ligating sequences comprising an adaptor onto each member of the population of flushed-ended fragments to generate a population of fragments containing terminal adaptor sequences;
optionally size-fractionating the population via gel electrophoresis to obtain a template library restricted to the size range desired;
subjecting the population of fragments containing terminal adaptor sequences to DNA amplification with a primer to generate a population of double-stranded molecules having a 5' single-stranded terminus;
and denaturing the population of double-stranded molecules having a 5' single-stranded terminus to generate a population comprising the nucleic acid hybridization probe,
wherein the primer comprises a single-stranded molecule having the following structure: 5'-S-L-A-3'
wherein
S is a signaling domain consisting of a nucleic acid having at least one chemically modified nucleobase covalently attached to a label;
L is a linker comprising a moiety having at least one abasic site consisting of iSp3, iSp9 or iSp18; and
A comprises a nucleic acid sequence corresponding to the adaptor sequence at the terminus of each member of the population of fragments containing terminal adaptor sequences and having the appropriate strand polarity to permit primer extension on the population of fragments containing terminal adaptor sequences using DNA amplification,
wherein the label consists of a member selected from a group consisting of a fluorescent moiety, a chemiluminescent moiety, an enzyme, substrate for an enzyme, an antigen for an antibody, and a ligand for at least one ligand-binding molecule.

8. The method of claim 7, wherein the signaling domain comprises a plurality of chemically modified nucleobases covalently attached to labels.

9. The method of claim 8, wherein the plurality of chemically modified nucleobases covalently attached to labels comprises a chemically modified nucleobase covalently attached to a label spaced every 3-12 nucleotides.

10. The method of claim 8, wherein the labels comprise two or more labels having discrete optical or spectroscopic properties.

11. The method of claim 7, wherein the nucleic acid target sequence comprises a genomic DNA sequence, a cDNA sequence or an RNA sequence.

12. The method of claim 7, wherein the nucleic acid target sequence comprises a nucleic acid sequence lacking repetitive sequence elements.

13. A method of detecting a nucleic acid target sequence in a sample, comprising:
obtaining the sample containing the nucleic acid target sequence;

contacting the sample with the nucleic acid hybridization probe of claim 1; and visualizing the hybridization signal.

14. The method of claim 13, further comprising:
performing DNA amplification on the nucleic acid target sequence using polymerase chain reaction (PCR), and
visualizing the hybridization signal by quantitative PCR, real-time PCR, PNA clamp-mediated PCR or digital PCR.

15. The method of claim 13, wherein the nucleic acid target sequence comprises a nucleic acid sequence lacking repetitive sequence elements.

16. The method of claim 13, further comprising immobilizing the sample onto a substrate, wherein the substrate comprises a particle, a membrane, a microarray substrate, or a FISH assay substrate.

17. A kit comprising a set of chromosomal probes and optionally one or more reagents selected from the group consisting of a slide, phosphate buffered saline, hybridization buffer, 4,6-diamidino-2-phenylindole dihydrochloride, sodium chloride-sodium citrate solution, fixative, ethanol, non-ionic detergent, and denaturation buffer,
wherein the set of chromosomal probes comprises the nucleic acid hybridization probe of claim 1,
wherein the probes are labeled such that each probe can be distinctly visualized after hybridization to a biological sample.

18. The kit of claim 17, wherein the set of chromosomal probes comprises one or more isolated nucleic acid sequences specific for a genetic locus.

19. The kit of claim 18, wherein the genetic locus comprises at least one member selected from the group consisting of EGFRv3, CDKN2A/p16 (9p21) and p53 (17p13.1).

20. The kit of claim 17, wherein the set of chromosomal probes comprises at least one nucleic acid sequence lacking repetitive sequence elements.

21. A nucleic acid hybridization probe for detecting a nucleic acid target sequence, said nucleic acid hybridization probe consists of structure (I):

$$5'\text{-}S\text{-}L\text{-}A\text{-}H\text{-}3' \qquad (I),$$

wherein
H is a hybridization domain,
A is an adaptor,
L is a linker, and
S is a signaling domain,
wherein
the hybridization domain comprises a nucleic acid sequence having complementarity to the nucleic acid target sequence,
the adaptor comprises a nucleic acid sequence,
the linker comprises a moiety having at least one abasic site consisting of iSp3, iSp9 or iSp18,
the signaling domain consists of a nucleic acid having at least one chemically modified nucleobase covalently attached to a label,
wherein the hybridization domain comprises a 3'-OH terminus and
wherein the nucleic acid target sequence comprises a genetic locus associated with a cancer selected from a group consisting of prostate cancer, adrenocortical cancer, biliary cancer, breast cancer, ovarian cancer, endometrial (uterine) cancer, cervical cancer, colorectal cancer, esophageal cancer, gall bladder cancer, gastric cancer, glioma, glioblastoma, head and neck cancer, lung cancer, bladder cancer, pancreatic cancer, gastric cancer, and salivary gland cancer.

22. The nucleic acid hybridization probe of claim 21, wherein the genetic locus comprises at least one member selected from a group consisting of EGFRv3, CDKN2A/p16 (9p21) and p53 (17p13.1).

* * * * *